(12) United States Patent
Buck, Jr.

(10) Patent No.: US 7,751,864 B2
(45) Date of Patent: Jul. 6, 2010

(54) SYSTEM AND METHOD FOR OPERATING AN ELECTROCHEMICAL ANALYTE SENSOR

(75) Inventor: Harvey B. Buck, Jr., Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 623 days.

(21) Appl. No.: 11/680,963

(22) Filed: Mar. 1, 2007

(65) Prior Publication Data

US 2008/0214910 A1 Sep. 4, 2008

(51) Int. Cl.
*A61B 5/05* (2006.01)

(52) U.S. Cl. .................. 600/345; 600/347; 600/365; 205/779; 204/403.01

(58) Field of Classification Search ......... 600/345–350, 600/365–366; 205/775; 204/193–194, 400, 204/401, 403.01
See application file for complete search history.

(56) References Cited

U.S. PATENT DOCUMENTS

| | | | |
|---|---|---|---|
| 885,476 A | 4/1908 | Hogrebe et al. | |
| 4,919,770 A * | 4/1990 | Preidel et al. | 205/780.5 |
| 5,025,219 A * | 6/1991 | Gaspard | 324/447 |
| 5,097,834 A | 3/1992 | Skrabal | |
| 5,193,545 A | 3/1993 | Marsoner et al. | |
| 5,411,647 A | 5/1995 | Johnson et al. | |
| 5,494,831 A * | 2/1996 | Kindler | 205/777.5 |
| 5,882,494 A | 3/1999 | Van Antwerp | |
| 6,091,976 A | 7/2000 | Pfeiffer et al. | |
| 6,175,752 B1 | 1/2001 | Say et al. | |
| 6,434,409 B1 | 8/2002 | Pfeiffer et al. | |
| 6,591,126 B2 | 7/2003 | Roeper et al. | |
| 6,721,587 B2 | 4/2004 | Gough | |
| 7,022,071 B2 | 4/2006 | Schaupp et al. | |
| 2004/0111017 A1 | 6/2004 | Say et al. | |
| 2004/0137547 A1 | 7/2004 | Shah et al. | |
| 2004/0168934 A1 | 9/2004 | Schauup et al. | |
| 2004/0219664 A1 | 11/2004 | Heller et al. | |

(Continued)

FOREIGN PATENT DOCUMENTS

EP 0247850 B1 4/1993

(Continued)

OTHER PUBLICATIONS

Ward et al., "A Fully Implantable Subcutaneous Glucose Sensor Arrary: Enhanced Accuracy from Multiple Sensing Units and a Median-Based Algorithm," Diabetes Technology & Therapeutics, vol. 5, No. 6, 2006 (pp. 943-952).

(Continued)

*Primary Examiner*—Robert L Nasser
*Assistant Examiner*—Michael D'Angelo
(74) *Attorney, Agent, or Firm*—Barnes & Thornburg LLP

(57) ABSTRACT

A method of operating an electrochemical analyte sensor having one or more electrodes may comprise applying a time-varying input signal to at least one of the one or more electrodes, monitoring a time-varying output signal produced by the sensor in response to application of the time-varying input signal, determining a complex impedance of the sensor based on the time-varying input and output signals, and determining from the complex impedance information relating to operation of the sensor.

20 Claims, 25 Drawing Sheets

U.S. PATENT DOCUMENTS

| | | | |
|---|---|---|---|
| 2005/0090607 | A1 | 4/2005 | Tapsak et al. |
| 2005/0103625 | A1 | 5/2005 | Rhodes et al. |
| 2007/0170073 | A1 | 7/2007 | Wang et al. |
| 2007/0173712 | A1* | 7/2007 | Shah et al. .................. 600/347 |
| 2007/0299617 | A1 | 12/2007 | Willis |

FOREIGN PATENT DOCUMENTS

| | | |
|---|---|---|
| WO | WO 01021827 | 3/2001 |
| WO | WO 2004007756 | 1/2004 |
| WO | WO 2005032362 | 4/2005 |

OTHER PUBLICATIONS

Feldman et al., "A Continuous Glucose Sensor Based on Wired Enzyme Technology—Results from a 3-Day Trial in Patients with Type 1 Diabetes," Diabetes Technology & Therapeutics, vol. 5, No. 5, 2006 (pp. 769-779).

Caster et al., "Mass Transport and Reaction Kinetic Parameters Determined Electrochemically for Immobilized Glucose Oxidase," Biochemistry 23, 1984 (pp. 2203-2210).

Leypoldt et al., "Model of a Two-Substrate Enzyme Electrode for Glucose," Anal. Chem, 56, 1984 (pp. 2896-2904).

Wang et al., "Oxygen-Rich Oxidase Enzyme Electrodes for Operation in Oxygen-Free Solutions," J. Am. Chem. Soc. 120, 1998 (pp. 1048-1050).

Nowak et al., "Biocompatibility of MPC: in vivo evaluation for clinical application," J. Artif. Organs 3, 2000 (pp. 39-46).

Schoemaker et al., The SCGM1 System: Subcutaneous Continuous Glucose Monitoring Based on Microdialysis Technique, Diabetes Technology & Therapeutics, vol. 5, No. 4, 2003 (pp. 599-608).

Gamry Instruments Electrochemical Measurement Systems hardware Operator's Manuals (5 pages).

R.K. Shervedani et al., A Novel Method for Glucose Determination Based on Electrochemical Impedance Spectroscopy Using Glucose Oxidase Self-Assembled Biosensor, Bioelectrochemistry 69 (2006) 201-208 (8 pages).

E. Souteyrand et al., Direct Detection of Biomolecules by Electrochemical Impedance Measurements, Sensors and Actuators B. 20 (19944) 63-69 (7 pages).

Tang et al., "New amperometric and potentiometric immunosensors based on gold nanoparticles/tris (2,2'-bipyridyl) cobalt(III) multilayer films for hepatitis B surface antigen determinations," Biosensors BioElectronics 211 (2005) 539-548 (10 pages).

Polk et al., "Ag/AgC1 microelectrodes with improved stability for microfluidics," Sensors and Actuators B 114 (2006) 239-247 (9 pages).

Gufler et al., "Highly robust lipid membranes on crystalline S-layer supports investigated by electrochemical impedance spectroscopy," Biochimica et Biophysica Acta 1661 (2004) 154-165 (12 pages).

Notification of Transmittal of the International Preliminary Report on Patentability and the PCT International Preliminary Report on Patentability for PCT/EP2008/001608 dated Jun. 9, 2009 (5 pages).

* cited by examiner

SYSTEM AND METHOD FOR OPERATING AN ELECTROCHEMICAL ANALYTE SENSOR

FIELD OF THE INVENTION

The present invention relates generally to analyte sensors, and more specifically to systems and techniques for operating analyte sensors.

BACKGROUND

Electrochemical analyte sensors for in vivo measurements of one or more analytes within a human or animal are known. Such sensors typically include one or more electrodes that come into contact with fluid and/or tissue of the human or animal. Electronic circuitry external to the human or animal is used to control operation of the sensor by sending one or more electrical signals to the one or more sensor electrodes and monitoring an electrochemical reaction that takes place between the fluid/tissue and at least one of the one or more electrodes. It is desirable with such sensors to make accurate analyte measurements. It is also desirable to determine information relating to the operation of such sensors in the environment containing the analyte, and to also determine diagnostic information relating to sensor operation.

SUMMARY

The present invention may comprise one or more of the features recited in the attached claims, and/or one or more of the following features and combinations thereof. A method of operating an electrochemical analyte sensor having one or more electrodes may comprise applying a time-varying input signal to at least one of the one or more electrodes and monitoring a time-varying output signal produced by the sensor in response to application of the time-varying input signal. A complex impedance of the sensor based on the time-varying input and output signals may be determined. From the complex impedance, information relating to operation of the sensor may be determined.

Determining from the complex impedance information relating to operation of the sensor may comprise determining at least one measured value of an analyte to which the sensor is exposed based, at least in part, on the complex impedance. The method may further comprise applying a DC input signal to the at least one of the one or more electrodes, and monitoring a DC output signal produced by the sensor in response to the application of the DC input signal. Determining at least one measured value of the analyte may comprise determining the at least one measured value of the analyte based on the complex impedance and on the DC output signal. Determining at least one measured value of an analyte to which the sensor is exposed may comprise selecting a mathematical model of the sensor having a number of model components, fitting values of the complex impedance to the mathematical model of the sensor to determine values of the number of model components, identifying one or a functional combination of the number of model components having a response over time that, when combined with the DC output signal, produces a sensor response that has minimal undesirable variations in magnitude over time, and computing the at least one measured value of the analyte based on values of the identified one or functional combination of the number of model components and on the DC output signal. The method may further comprise identifying another one or a functional combination of the model components having a response over time that is substantially insensitive to variations in analyte concentration and sensor sensitivity, identifying as stable only ones of the one or a functional combination of the number of model components for which the values of corresponding ones of the another one or a functional combination of the model components fall within a range of response values, and using only the stable ones of the one or a functional combination of the number of model components to compute the at least one measured value of the analyte. Applying a time-varying input signal to at least one of the one or more electrodes may comprise applying the time-varying input signal at a number of different frequencies.

Determining at least one measured value of an analyte to which the sensor is exposed may comprise selecting a mathematical model of the sensor having a number of model components, fitting values of the complex impedance to the mathematical model of the sensor to determine values of the number of model components, identifying one or a functional combination of the number of model components having a response over time that produces a sensor response that has minimal undesirable variations in magnitude over time, and computing the at least one measured value of the analyte based on values of the identified one or functional combination of the number of model components. The method may further comprise identifying another one or a functional combination of the model components having a response over time that is substantially insensitive to variations in analyte concentration and sensor sensitivity, identifying as stable only ones of the one or a functional combination of the number of model components for which the values of corresponding ones of the another one or a functional combination of the model components fall within a range of response values, and using only the stable ones of the one or a functional combination of the number of model components to compute the at least one measured value of the analyte. Applying a time-varying input signal to at least one of the one or more electrodes comprises applying the time-varying input signal at a number of different frequencies.

Determining from the complex impedance information relating to operation of the sensor may comprise determining whether an output response of the sensor is stable. Determining whether an output response of the sensor is stable may comprise selecting a mathematical model of the sensor having a number of model components, fitting values of the complex impedance to the mathematical model of the sensor to determine values of the number of model components, identifying one or a functional combination of the model components having a response over time that is substantially insensitive to variations in analyte concentration and sensor sensitivity, and identifying as stable only sensor output response samples for which the values of corresponding ones of the one or a functional combination of the model components fall within a range of response values.

The method may further comprise producing a signal when the output response of the sensor is not stable. Producing a signal when the output response of the sensor is not stable may comprise selecting a mathematical model of the sensor having a number of model components, fitting values of the complex impedance to the mathematical model of the sensor to determine values of the number of model components, identifying one or a functional combination of the model components having a response over time that is substantially insensitive to variations in analyte concentration and sensor sensitivity, and producing the signal if a number of values of the one or functional combination of the model components fall outside of a range of constant response values.

The method may further comprise executing a sensor calibration procedure if the output response of the sensor is not stable. Executing a sensor calibration procedure if the output response of the sensor is not stable may comprise selecting a mathematical model of the sensor having a number of model components, fitting values of the complex impedance to the mathematical model of the sensor to determine values of the number of model components, identifying one or a functional combination of the model components having a response over time that is substantially insensitive to variations in analyte concentration and sensor sensitivity, and executing the sensor calibration procedure if a number of values of the one or functional combination of the model components fall outside of a range of constant response values.

Determining from the complex impedance information relating to operation of the sensor may comprise determining from the complex impedance at least one characteristic of the sensor. The at least one characteristic of the sensor may include a capacitance of the sensor.

Determining from the complex impedance information relating to operation of the sensor may comprise determining from the complex impedance at least one parameter relating to operation of the sensor in an environment containing an analyte. The at least one parameter relating to operation of the sensor in an environment containing the analyte may include an electrical conductivity of the environment containing the analyte.

Determining from the complex impedance information relating to operation of the sensor may comprise determining from the complex impedance diagnostic information relating to reliability of analyte measurement information produced by the sensor. Determining from the complex impedance diagnostic information relating to reliability of analyte measurement information produced by the sensor may comprises comparing the complex impedance to an impedance threshold, and determining that an electrically conductive path associated with the sensor has failed if the complex impedance is greater than the impedance threshold.

A method of operating an electrochemical analyte sensor having one or more electrodes may comprise applying a time-varying input signal to at least one of the one or more electrodes and monitoring a time-varying output signal produced by the sensor in response to application of the time-varying input signal. A complex impedance of the sensor may be determined based on the time-varying input and output signals. Measured values of an analyte to which the sensor is exposed may be determined based, at least in part, on the complex impedance.

Applying a time-varying input signal to at least one of the one or more electrodes may further include applying at the same time a DC input signal to the at least one of the one or more electrodes, and may further comprise monitoring a DC output signal produced by the sensor in response to application of the DC input signal. Computing a measured value of an analyte to which the sensor is exposed may comprise selecting a model of the sensor having model components, fitting values of the complex impedance to the model of the sensor to determine complex values of the model components, determining one or a functional combination of the model components that, when the complex values of the one or functional combination of the model components are mathematically combined with the DC output signal, compensates for an effect on the measured values of the analyte of at least one undesirable characteristic of the DC output signal of the sensor, and computing the measured values of the analyte based the DC output of the sensor and the one or functional combination of the complex values of the model components. Selecting a model of the sensor may comprise selecting an equivalent mathematical circuit model of the sensor having model components in the form of mathematical electrical components that are interconnected to define the circuit model. Fitting the values of the complex impedance to the model of the sensor may comprise mathematically fitting the values of the complex impedance to a number of mathematical equations defining the equivalent mathematical circuit model to determine a corresponding set of values for each of the mathematical electrical components.

Determining one or a functional combination of the model components may comprise determining one or a functional combination of the model components that, when the values of the one or functional combination of the model components are combined with the DC output signal of the sensor, compensates for an effect on the measured values of the analyte of a sensitivity drift of the DC output signal of the sensor over time.

Computing the measured values of the analyte may comprise performing a statistical procedure on the DC output signal of the sensor and on the values of the one or functional combination of the model components. Computing the measured values of the analyte may comprise performing a principle component statistical procedure on the values of the one or functional combination of the model components to determine a number of principle components, fitting at least some of the principle components to a set of principle component model equations that model the measured value of the analyte, and applying the DC output signal of the sensor to the set of principle component model equations and solving for the measured values of the analyte.

Computing the measured values of the analyte may comprise fitting at least some of the values of the one or functional combination of the model components to a set of empirical model equations that model the measured value of the analyte, and applying the DC output signal of the sensor to the set of empirical model equations and solving for the measured values of the analyte.

A method of operating an electrochemical analyte sensor having one or more electrodes may comprise applying a time-varying input signal to at least one of the one or more electrodes, varying a frequency of the time-varying input signal over a spectrum of frequencies, and monitoring a time and frequency varying output signal produced by the sensor in response to application of the time and frequency varying input signal. A corresponding spectrum of complex impedance values of the sensor may be determined based on the time and frequency varying input and output signals.

The method may further comprise processing at least a portion of the spectrum of complex impedance values to determine at least one characteristic of the sensor.

The method may further comprise processing at least a portion of the spectrum of complex impedance values to determine at least one parameter relating to operation of the sensor in an environment containing an analyte.

Varying a frequency of the time-varying input signal over a spectrum of frequencies may comprise incrementally increasing the frequency of the time-varying input signal throughout the spectrum of frequencies.

Varying a frequency of the time-varying input signal over a spectrum of frequencies may comprise incrementally decreasing the frequency of the time-varying input signal throughout the spectrum of frequencies.

Varying a frequency of the time-varying input signal over a spectrum of frequencies may comprise providing the time-varying input signal as a multi-frequency, time-varying input signal that includes frequencies that are within the spectrum of frequencies.

Varying a frequency of the time-varying input signal over a spectrum of frequencies may comprise providing the time-varying input signal as a complex mixture of frequencies within the spectrum of frequencies in a manner that allows a magnitude of the time-varying input signal to remain small.

The method may further comprise determining from the spectrum of complex impedance values a characteristic of the sensor or of a sensor circuit containing the sensor. Determining from the spectrum of complex impedance values a characteristic of the sensor or of a sensor circuit containing the sensor may comprise relating one or more of the complex impedance values to the characteristic of the sensor.

Determining from the spectrum of complex impedance values a characteristic of the sensor or of a sensor circuit containing the sensor may comprise performing a statistical procedure on at least a portion of the spectrum of complex impedance values to determine a state of the characteristic of the sensor. Determining from the spectrum of complex impedance values a characteristic of the sensor or of a sensor circuit containing the sensor may comprise fitting at least a portion of the spectrum of complex impedance values to an equivalent sensor circuit model including at least one electrical component having a component value that is indicative of one or more characteristics of the sensor circuit. Determining from the spectrum of complex impedance values a characteristic of the sensor or of a sensor circuit containing the sensor may comprise fitting at least a portion of the spectrum of complex impedance values to an equivalent sensor circuit model including at least one model component having a component value, and performing a statistical procedure on the at least one model component value to determine the characteristic of the sensor.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1A:
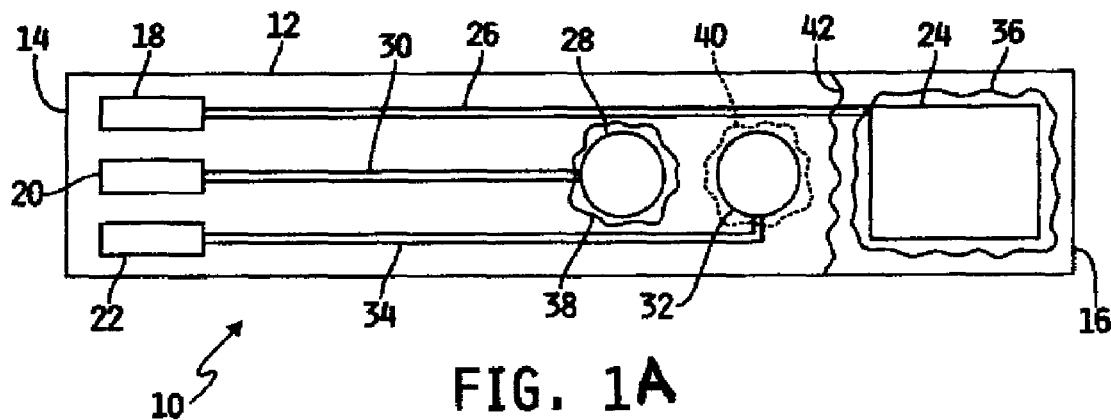
FIG. 1A is a top plan view of one illustrative embodiment of an electrochemical analyte sensor.

Referring now to FIG. 1A, a top plan view of one illustrative embodiment of an electrochemical analyte sensor 10 is shown. In the illustrated embodiment, the sensor 10 includes an elongated substrate 12 having a number of sensor electrodes formed thereon. Illustratively, the substrate 12 may be flexible, and may accordingly be formed of any conventional biocompatible material or compound such as a polymer, although the substrate 12 may alternatively be rigid or semi-rigid, and may be formed of suitable rigid or semi-rigid materials. The elongated substrate 12 has a proximal end 14 and an opposite distal end 16, wherein the distal end 16 may be transcutaneously or subcutaneously inserted into a body of a living animal such as a human. The sensor 10 may be configured, for example, to be subcutaneously or transcutaneously implanted into tissue or a blood vessel of an animal such as a human.

A number of electrical contacts 18, 20 and 22 are formed on the substrate 12 near the proximal end 14 thereof, and each are electrically connected to a corresponding electrode formed near the distal end 16 of the substrate 12 via an electrical trace. For example, the electrical contact 18 is electrically connected to a reference electrode 24 via an electrical trace 26, the electrical contact 20 is electrically connected to a reference electrode 28 via an electrical trace 30, and the electrical contact 22 is electrically connected to a counter electrode 32 via an electrical trace 34. The various electrical contacts 18, 20 and 22, electrodes 24, 28 and 32, and electrical traces 26, 30 and 34, may all be formed on the surface of the substrate 12 via conventional techniques. In one embodiment, for example, the electrical contacts, electrodes and electrical traces may be formed on the substrate 12 by sputtering a suitable conductive film, e.g., gold, onto the surface of the substrate 12, and then selectively removing areas of the deposited film to form the electrical contacts, electrodes and electrical traces. Any conventional technique may be used to selectively remove areas of the deposited film to define the electrical contacts, electrodes and electrical traces, and examples of such conventional techniques include, but are not limited to, laser ablation, chemical etching, dry etching, and the like.

The sensor 10 may further include a reagent layer 36 formed on the working electrode 24 as is known in the art. One example reagent layer 36 may comprise a conventional glucose oxidase formulation that is dispensed onto the working electrode 24 as illustrated in FIG. 1. Another example reagent layer 36 may comprise a conductive carbon ink formulation, e.g., acheson colloids, manganese dioxide, and a solvent such as butyl glycol that is dispensed onto the working electrode 24 as illustrated in FIG. 1. It will be appreciated that other conventional reagent layers may alternatively or additionally be formed on the working electrode 24. A conventional silver/silver chloride ink formulation, e.g., Ercon DPM 68, may be formed, e.g., dispensed, on the reference electrode 28. Optionally, a reagent layer 40 may be formed on the counter electrode 32, and such a reagent layer 40 may or may not be identical to the reagent layer 36 formed on the working electrode 24. Alternatively, the reagent layer 40 may be omitted, and the conductive film used to form the counter electrode 32 may, by itself, define the counter electrode 32. A resistive layer or membrane 42 may further be formed over the combination working electrode 24 and reagent layer 36. A resistive layer or membrane 42 may be formed of a conventional biocompatible polymer that hinders or resists diffusion of enzymes from the working electrode 24, hinders or resists absorption of protein, or the like. In one illustrative example, the resistive layer or membrane 42 may be conventional hydrophilic polyurethane, Methacroylphosphorochoine-CO-Butyl Methacrylate (MPC) or the like. One example hydrophilic polyurethane that may be used to form such a resistive layer or membrane 42 is described in U.S. Pat. No. 6,509,148 to Cha et al., the disclosure of which is incorporated herein by reference. One example MPC that may be used to form the resistive layer or membrane 42 is commercially available from NOF Corporation of Tokyo, Japan and marketed under the trademark LIPIDURE®. In any case, the resistive layer or membrane 42 ideally hinders or resists protein absorption while also providing minimal diffusion limitation for glucose. It will be understood that for purposes of this disclosure, the sensor 10 may include more or fewer electrodes, and more or fewer layers and/or membranes deposited over any one or more of the electrodes.

Figure 1B:
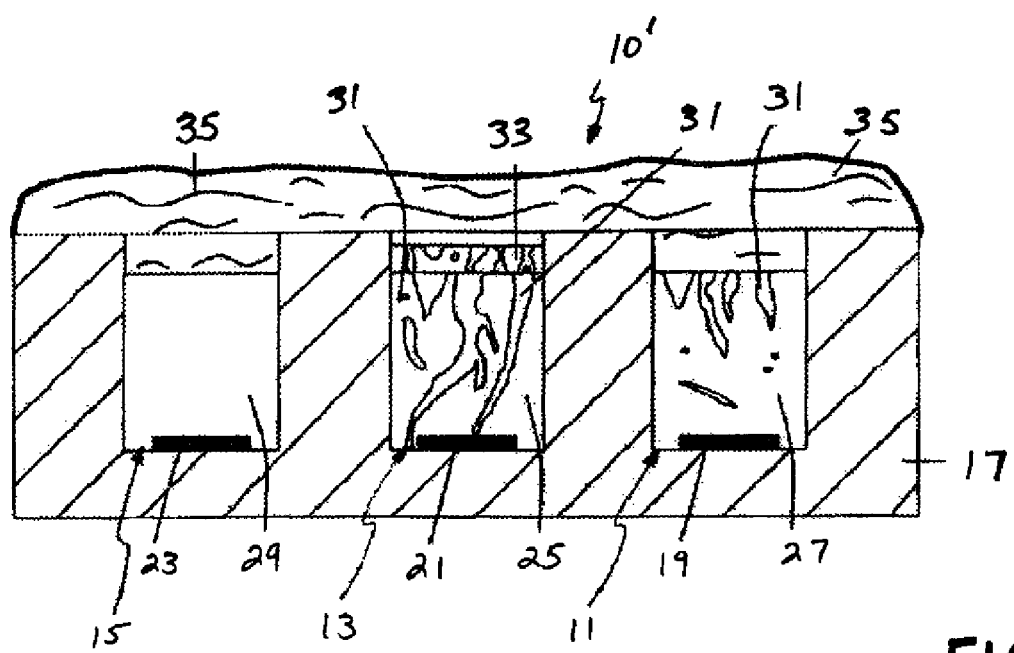
FIG. 1B is a cross-sectional view of another illustrative embodiment of an electrochemical analyte sensor.

Referring now to FIG. 1B, a cross-sectional view of another illustrative embodiment of an electrochemical analyte sensor 10' is shown. In the illustrated embodiment, the sensor 10' is an amperometric sensor configured to be implantated into the living body of a human or animal to measure the concentration of an analyte in a body fluid of the human or animal. The sensor 10' has a counter electrode 11, a working electrode 13 and a reference electrode 15 which are arranged on a support member 17 made of a plastic material, e.g., polyimide. Each electrode 11, 13, 15 comprises a corresponding contact pad 19, 21, 23 which is illustratively provided in the form of a metallic film, e.g. a gold film, with a thickness of, for example, 50 nm to 150 nm. In an alternative embodiment, a combined counter/reference electrode may be used instead of separate counter and reference electrodes 13, 15. One example of a suitable counter/reference electrode is a silver/silver-chloride electrode.

The working electrode 13 further comprises a sensing layer 25 which is illustratively permeable for water and is arranged on the contact pad 21 of the working electrode 13. Illustratively, the sensing layer 25 comprises an immobilized enzyme capable of acting catalytically in the presence of the analyte to produce an electrical measurement signal. In one exemplary embodiment, a glucose oxidase is used as the enzyme to measure glucose as an analyte in a human body fluid, such as interstitial fluid or blood.

The sensing layer 25 may be applied, for example, as a paste onto the support member 17 to cover the contact pad 21 of the working electrode 13. The paste may be made, for example, by mixing carbon particles, the enzyme and a polymeric binder. In this way, the immobilized enzyme is distributed substantially equally throughout the sensing layer 25, and illustratively the enzyme concentration may differ by less than 20%, or less than 10%, between the upper surface and the lower surface of the sensing layer 25. As the analyte can diffuse into the porous sensing layer 25, the electrical measurement signal is created not just in the upper surface sensing layer 25 which faces away from the contact pad 21, but also in an extended volume of the sensing layer 25. Therefore, rather low oxygen concentrations are sufficient to saturate the sensor 10' with oxygen to enable precise measurements.

The sensing layer 25 of the illustrated example sensor 10' has a thickness of approximately 30 µm. In one embodiment, the sensing layer 25 should have a thickness of at least 5 µm, and an alternative embodiment at least 10 µm, in order to provide a sufficiently large volume of the sensing layer 25 for the creation of the electrical measurement signal. It has been observed that thicknesses of the sensing layer 25 of more than 100 µm generally do not provide additional benefits. A sensing layer 25 thickness of 20 µm to 70 µm is generally sufficient to produce desirable results. The sensing layer 25 is arranged in a depression of the support member 17. In this way, it is somewhat protected by lateral walls of the support member 17 from damage that may occur during the implantation process. Furthermore, the lateral surfaces of the sensing layer 25 can be connected to the support member 17 and thereby ensure that analyte molecules can diffuse only through the sensing layer's upper surface into the sensing layer 25. Alternatively, other conventional techniques and/or structures may be used to make the lateral surfaces of the sensing layer 25 impervious to water in this example.

In similar fashion, the contact pads 19, 23 of the counter electrode 11 and the reference electrode 15 are covered with water-permeable layers 27, 29 which may also be applied in the form of a paste. In the illustrated embodiment, the layers 27, 29 of the counter electrode 11 and the reference electrode 15 contain no enzyme. Like the sensing layer 25, layers 27 and 29 may also comprise carbon particles and a polymeric binder. Whereas porosity enhancing particles 31, such as carbon nanotubes, have been added to the pastes for the sensing layer 25 and the layer 27 in the illustrated embodiment, such porosity enhancing particles 31 were not added to the layer 29.

As enzyme is substantially distributed throughout the entire sensing layer 25, oxygen saturation can be maintained even if much higher analyte concentrations are present at the upper surface of the sensing layer 25 than is feasible for known sensors. The sensing layer 25 of the sensor 10' of the illustrated embodiment is therefore covered by a diffusion barrier which hinders diffusion of analyte molecules only to such an extent that after implantation into the living body of a human or animal the analyte concentration on the upper surface of the sensing layer 25 is at most ten times lower than in the body fluid surrounding the implanted sensor 10. In one alternative embodiment, the sensing layer 25 is covered by a diffusion barrier that hinders diffusion of analyte molecules such that the analyte concentration on the upper surface of the sensing layer 25 is at most five times lower than in the body fluid surrounding the implanted sensor 10', and in another alternative embodiment, at most three times lower. In the example shown, the diffusion barrier comprises several distinct layers 33, 35 contributing to the diffusion resistance of the diffusion barrier against diffusion of analyte molecules.

The diffusion barrier is permeable for the analyte and prevents enzyme from leaking out of the sensing layer 25. In the example shown, the diffusion barrier comprises as a first layer an electrically conductive enzyme-free layer 33 which comprises carbon particles and a polymeric binder and has a thickness of less than a third of the thickness of the sensing layer 25. It may be, for example, about 1 µm to 3 µm thick. Like the sensing layer 25 the enzyme-free layer 33 may be applied as a paste, which may differ from the paste used to form the sensing layer 25 only in that no enzyme is added to it.

The diffusion barrier also comprises a layer 35 which prevents large molecules from clogging the pores of the sensing layer 25. The layer 35 may be a dialysis layer which can be provided as a membrane made of cellulose and/or a polymer material. Such a dialysis layer is also an enzyme-free layer and may be applied directly on top of the sensing layer 25 or, as shown in FIG. 1B, on top of the electrically conductive enzyme-free layer 33. It is desirable that the dialysis layer does not hinder analyte diffusion, or hinders analyte diffusion as little as possible. In one illustrative embodiment, the layer 35 has an effective diffusion coefficient for the analyte which is at most ten times lower than the diffusion coefficient of the analyte in water, an in an alternative embodiment at most five times lower than the diffusion coefficient of the analyte in water. The layer 35 can be applied as a solid film or applied as a polymer solution which hardens into a dialysis membrane in-situ.

Dialysis membranes are often characterized by their molecular weight cut off (MWCO) which depends on the pore size. The MWCO describes the molecular weight at which a compound will be 90% retained following of a night (17-hour) of dialysis. In one illustrative embodiment, the layer 35 has a MWCO of less than 10 kDalton (kD), in one alternative embodiment less than 7 kD, and in another alternative embodiment less than 5 kD. It is to be understood, however, that MWCOs stated for dialysis layers apply strictly to globular molecules such as most proteins. More linear molecules may be able to pass through the pores of a dialysis layer, even if their molecular weight exceeds the stated MWCO.

Instead of, or in addition to, a dialysis membrane the diffusion barrier may also comprise a polymer layer made of a polymer having a zwitterionic structure to protect the sensing layer 25 and any porous layer 33 from ingression of proteins. A zwitterionic structure enables the rapid uptake of polar protic solvents, in particular water, and such analytes as glucose dissolved within. Hence, polymers having a zwitterionic structure attached to a polymeric backbone are impermeable for proteins but hinder diffusion of analytes, such as glucose, very little. A well-known example for such a polymer is poly(2-methacryloyoloxyethyl phoshorylcholine-co-n-butyl metha-crylate) (MPC for short). In one illustrative embodiment, the MPC polymer layer 35 may be applied as a polymer solution comprising ethanol or distilled water and at least 5 wt. % MPC, and in an alternative embodiment at least 10 wt. % MPC.

The diffusion barrier, and particularly the polymer layer 35 which it comprises, protects the sensor 10' from mechanical damage during the implantation process, prevents enzyme from leaking out of the sensing layer 25 into surrounding tissue, and prevents large molecules from clogging pores of the sensing layer 25. It is possible to mix a polymer having a zwitterionic structure like MPC with another polymer, for example polyurethane or typical constituents of dialyse membranes, in order to tune physical properties of the polymer layer 35.

The sensing layer 25 in the example shown in FIG. 1B contains porous particles 31 to increase its porosity and thereby ease diffusion of analyte molecules into the sensing layer 25. Porous particles in this example are particles which have voids to adsorb water molecules. The porous particles 31 may be added to the paste from which the sensing layer 25 is formed, and cause voids in the layer 25 through which analyte molecules and water may pass. The porous particles 31 are bound with other particles of the paste by the polymeric binder. Carbon nanotubes, for example, are effective additives to increase the porosity of the sensing layer as they tend to form clews, which are only partially filled with carbon particles and binder, and which also increase the electrical conductivity of the sensing layer. Silica particles may additionally or alternatively be used as porous particles 31 to increase the porosity of the sensing layer 25.

If silica or similar porous particles are used, it is desirable to use material with a particle size distribution such that the maximum particle size is less than the thickness of the sensing layer 25. In one illustrative embodiment, the porous particles are at least 1 μm, and in an alternative embodiment at least 5 μm. Considering a sensing layer thickness of around 20 μm to 50 μm, silica FK 320 from Degussa provides adequate particle size, up to 15 μm. In one illustrative embodiment, less than 10% of this material is mixed into the paste, and in another illustrative embodiment less than 5%.

Whatever structure for increasing the porosity is used, the mixing of the enzyme with the paste will typically lead to a fraction of enzyme molecules being accessible to the analyte, either on the upper surface of the sensing layer 25, or at the channels in the vicinity of the additive particles within the sensing layer. The enzyme is immobilized by adsorption and entrapment in the working electrode 13. Entrapment depends not only on the sensing layer 25, but also on properties of the diffusion barrier, i.e. the layer 35, and of the optional enzyme-free layer 33. It is understood that in order to maintain the desirable distribution of enzyme within the working electrode 13, contact with solvent (water) should not lead to massive detachment of enzyme from the matrix and subsequent migration of enzyme molecules. Enzyme immobilization in the sensing layer can be enhanced by cross-linking, such as by cross-linking enzyme molecules as a chain. If these chains are too long, however, the enzyme is less effective. In one illustrative embodiment, enzyme molecules are linked together on average 3 to 10, in one alternative embodiment, on average 4 to 8, and in another alternative embodiment on average 5 to 7.

It is possible to add a cross-linking agent, i.e. glutaraldehyd solution, to the paste before drying. However, it is desirable to mix an already cross-linked enzyme into the paste. It is desirable to use an enzyme which forms a complex link with a hydrophilic partner. After being mixed into a paste which is less hydrophilic or even hydrophobic, as can be achieved by mixing carbon particles with suitable binders, the cross-linked enzyme sits in a local hydrophilic environment which contributes to its stability. Cross-linking an enzyme with a hydrophilic partner also enhances migration of hydrated analyte molecules towards the enzyme. Thus the wetting of the sensing layer 25 is accelerated, which shortens the wet-up time of the sensor 10' after implantation. As a specific example, glucose oxidase cross-linked with dextrane from Roche Diagnostics (Penzberg, Germany, Ident-No. 1485938001) has been found to have such a content of enzyme (approximately 16%) that enough activity (20 to 30 U/mg lyophylisate) can be preserved. Due to the high degree of hydrophilic dextrane in the complex, the aforementioned the sensing layer 25 has the properties just described.

By mixing already cross-linked enzyme with a sensing layer paste containing carbon nanotubes, the trait of the carbon nanotubes to wind up and form clews, which act as macroporous cage structures, is supported by the larger enzyme-dextrane chains, in particular by their aggregation. As a consequence, the cross-linking enzyme will assist in the formation of porous structures of the sensing layer 25.

The sensing layer 25 in the example shown comprises carbon particles with an average size of less than 1 μm, a polymeric binder, an enzyme and carbon nanotubes as porous particles. The porous particles are most effective to increase the porosity of the sensing layer if they are significantly larger than the carbon particles. In one illustrative embodiment, the porous particles measure at least 1 μm on average, and in an alternative embodiment they measure at least 5 μm on average. Typically the sensing layer 25 comprises 50 wt. % to 70 wt. % polymeric binder, 20 wt % to 40 wt. % carbon particles and 1 wt. % to 10 wt. %, but up to about 20 wt. %, porous particles such as carbon nanotubes or silica. Carbon nanotubes increase both the porosity and the electrical conductivity of the sensing layer 25. In the illustrated embodiment, multiwall carbon nanotubes (research grade, purity>95%) by Nanolab, Newton, Mass., of length 5 μm to 20 μm and an average outer diameter of 25 nm to 35 nm have been used. The binder is a thermoplastic resin, e.g. on the basis of an epoxy resin. Resins on the basis of a fluor carbon resin, particularly polytetrafluoroethylene or polystyrene, may also be used as binders.

The sensing layer 25 of the sensor shown in FIG. 1B is adapted and arranged in such a way that in operation, after implantation, the analyte concentration in the sensing layer 25 is highest at the upper surface, decreases with increasing distance from the upper surface, and is zero at the lower surface which touches the contact pad 21. The enzyme loading of the sensing layer 25, i.e., the amount of the enzyme immobilized therein, should be chosen with respect to the porosity and water-permeability of the sensing layer 25.

Other example implementations of the sensor 10 include, but are not limited to, those disclosed in WO 01/21827 and WO 2005/032362, both of which are assigned to the assignee of the subject disclosure and the disclosures of which are incorporated by reference, the continuous glucose monitoring sensor that is commercially available from Medtronic Minimed, Inc. and marketed under the trademark CGMS®, the continuous glucose monitoring sensor that is commercially available from DexCom, Inc. and marketed under the trademark STSTM, and a continuous monitoring sensor that has been announced by Abbott Diabetes Care under the trademarks Freestyle® Navigator®. The sensor 10 is, in any case, configured to produce one or more electrical signals that correspond to one or more analytes that may be present in the tissue and/or blood of an animal or human. Examples of analytes that the sensor 10 may be configured to detect include, but are not limited to, glucose, lactate, carbohydrates, cholesterol, and the like. In any case, references hereinafter to sensor 10 or to sensor 10' will, except for the specific examples provided in this disclosures, be understood as referring to any of the sensor embodiments just described.

Figure 2:
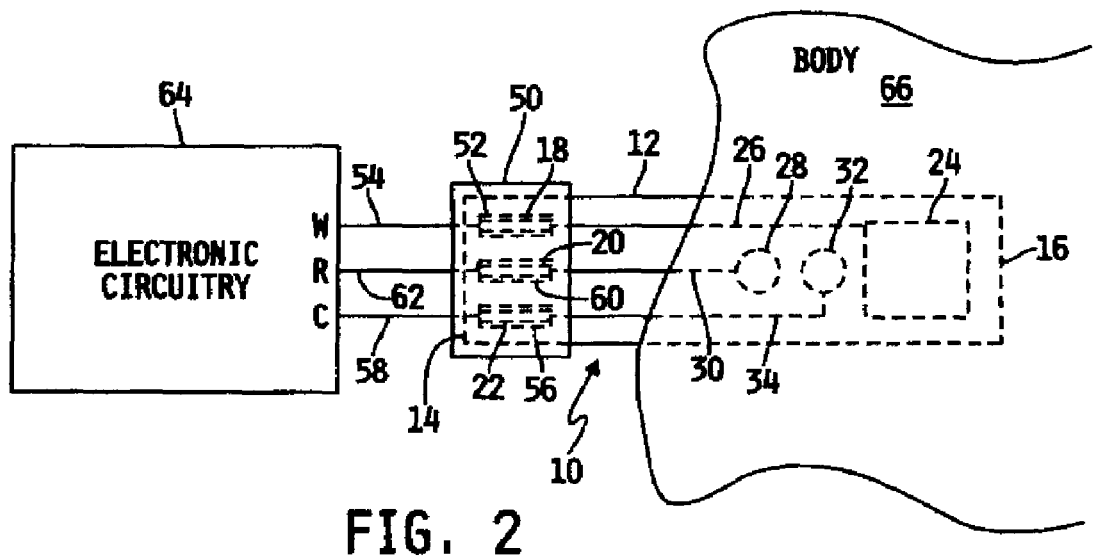
FIG. 2 is a diagrammatic illustration of the electrochemical analyte sensor of FIG. 1 having one end coupled to electronic circuitry and an opposite end extending into the body of a human or animal.

Referring now to FIG. 2, the electrochemical analyte sensor 10 is illustrated as having its proximal end 14 electrically coupled to electronic circuitry 64 via an electrical connector 50, and having its distal end 16 transcutaneously or subcutaneously inserted into a body 66 of an animal or human. In the illustrated embodiment, an electrical connector 50 includes a first electrical contact 52 that is electrically connected to a signal conductor 54, a second electrical contact 56 that is electrically connected to a signal conductor 58, and a third electrical contact 60 that is electrically connected to a signal conductor 62. The electrical contacts 52, 56 and 60 are arranged relative to the electrical connector 50 such that when the electrical connector 50 is advanced onto the proximal end 14 of the sensor 10, the electrical contacts 52, 56 and 60 align with, and electrically contact, corresponding ones of the electrical contacts 18, 20 and 22 that are formed on the substrate 12 of the sensor 10 near the distal end 14 thereof. More specifically, the electrical connector 50 is configured such that when the electrical connector 50 is advanced onto the proximal end 14 of the sensor 10 the electrical contact 52 of the electrical connector 50 aligns with, and electrically contacts, the electrical contact 18 formed on the substrate 12 of the sensor 10, the electrical contact 56 of the electrical connector 50 aligns with, and electrically contacts, the electrical contact 22 formed on the substrate 12 of the sensor 10, and the electrical contact 60 of the electrical connector 50 aligns with, and electrically contacts, the electrical contact 20 formed on the substrate 12 of the sensor 10. The signal conductors 54, 58 and 62 are electrically connected to the working electrode, W, counter electrode, C, and reference electrode, R, terminals respectively of an electronic circuit 64. Through the electrical connector 50, the W terminal of the circuit 64 is therefore electrically connected to the working electrode 24 of the sensor 10, the R terminal of the electronic circuit 64 is electrically connected to the reference electrode 28 of the sensor 10, and the C terminal of the electronic circuit 64 is electrically connected to the counter electrode 32 of the sensor 10. Generally, the electronic circuitry 64 is configured to provide one or more control signals to the sensor 10, and to monitor resulting measurement signals produced by the sensor to determine one or more analytes that may be present in the tissue or blood of the animal or human 66.

In alternative embodiments, the sensor 10 may include on-board wireless communication circuitry, in which case the electrical connector 50 may be omitted. In such embodiments, the on-board wireless communication circuitry may be configured to wirelessly communicate the raw sensor signals produced by the sensor 10 to off-board signal processing circuitry such as the electronic circuitry 64. In these embodiments, the electronic circuitry 64 is configured to process the raw sensor signals to determine sensor-related information, at least some of which may be of the type that will be described in greater detail hereinafter. In other embodiments, the sensor 10 may include additional on-board signal processing circuitry that is configured to process the raw sensor signals produced by the sensor 10, and to provide such processed sensor signal information to on-board wireless communication circuitry for wireless transmission to off-board electronic circuitry for further processing, storage, display or the like. In these embodiments, at least some of the processed sensor signal information that is determined by the on-board signal processing circuitry may be of the type that will be described in greater detail hereinafter. Various circuits and circuit components for wirelessly communicating raw and/or processed sensor data from the sensor 10 to off-board electronic circuitry are disclosed in co-pending U.S. patent application Ser. No. 11/742,998, and the disclosure of which is incorporated herein by reference.

Figure 3:
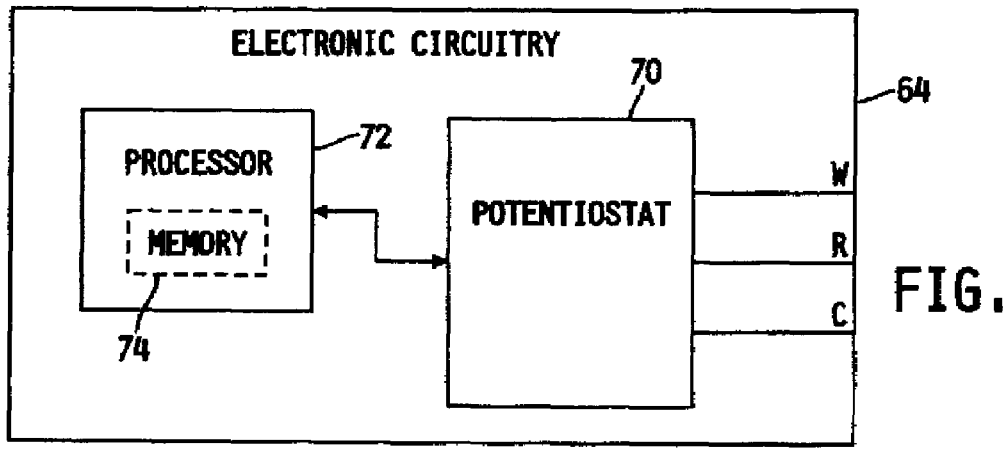
FIG. 3 is a block diagram of one illustrative embodiment of the electronic circuitry of FIG. 2.

Referring now to FIG. 3, one illustrative embodiment of the electronic circuitry 64 of FIG. 2 is shown. In the illustrative embodiment, the electronic circuitry 64 includes a conventional potentiostat 70, e.g., a Gamry PCI4/300 potentiostat, having inputs/outputs (I/Os) electrically connected to the W and R terminals respectively of the electronic circuitry 64. The potentiostat is electrically also electrically connected to a conventional processor 72 having a memory 74. The potentiostat 70 is configurable in a known manner to apply DC and/or AC voltages across, and DC and/or AC currents to, any of the W, R and C terminals and accordingly across any of the working, reference and counter electrodes 24, 28 and 32 respectively. The potentiostat is also configured in a known manner to monitor signals produced by or across any of the working, reference and counter electrodes 24, 28 and 32 respectively, and to provide signal information relating to such signals to the processor 72 for processing as will be described in greater detail herein. One or more software algorithms may be stored in the memory 74, and may be executable by the processor 72 to process sensor signals provided by the potentiostat 70 and that relate to the operation of the sensor 10. For example, the processor 72 is configured to process the sensor signals produced by the sensor 10, as will be described in detail hereinafter, to determine a complex impedance of the sensor 10. The processor 72 may further be configured to process the complex impedance information to determine other information relating to operation of the sensor 10 and/or its environment, and examples of such other information will be described hereinafter. The memory 74 further includes calibration data and other information that may be used by the one or more software algorithms. The processor 72 may additionally store information in the memory 74 that results from the processing of the sensor signals.

The electronic circuitry 64 is operable to determine a complex impedance of the sensor 10 by applying one or more time-varying input signals, e.g., voltage or current, to one or more electrodes of the sensor 10, monitoring or measuring one or more resulting time-varying output signals produced by the sensor 10 in response to the one or more time-varying input signals, and then computing the complex sensor impedance as a function of the one or more time varying input and output signals. Generally, the one or more time-varying input signals may be any time-varying signal that allows the complex impedance of the sensor circuit to be determined by measuring the time-varying response of the sensor circuit to the one or more applied time-varying input signals. For example, the electronic circuitry 64 may be configured to apply a time-varying input voltage to the sensor 10, to measure a resulting time-varying output current produced by the sensor 10, and to compute the complex impedance of the sensor 10 in a known manner based on measured values of the applied voltage and output current. As another example, the electronic circuitry 64 may be configured to apply a time-varying input voltage to the sensor 10, to measure a resulting time-varying output current produced by the sensor 10, and to compute the complex impedance of the sensor 10 in a known manner based on target or requested values of the applied voltage and measured values of the output current. As a further example, the electronic circuitry 64 may be configured to apply a time-varying input current to the sensor 10, to measure a resulting time-varying output voltage produced by the sensor 10, and to compute the complex impedance of the sensor 10 in a known manner based on target or requested values of the applied current and measured values of the output voltage. As still another example, the electronic circuitry 64 may be configured to apply a time-varying input current to the sensor 10, to measure a resulting time-varying output voltage produced by the sensor 10, and to compute the complex impedance of the sensor 10 in a known manner based on measured values of the applied current and the output voltage. In any case, the complex impedance information may then be used to augment or correct the conventional DC response of the sensor 10 prior to determining an analyte value based on the DC response, to provide a measurement signal independent of the sensor DC response from which an analyte value may be determined, to determine one or more properties of the environment to which the sensor 10 is exposed, to determine or assess the stability of the sensor, and/or as a basis for conducting one or more quality checks relating to the performance or integrity of the sensor.

Figure 4:
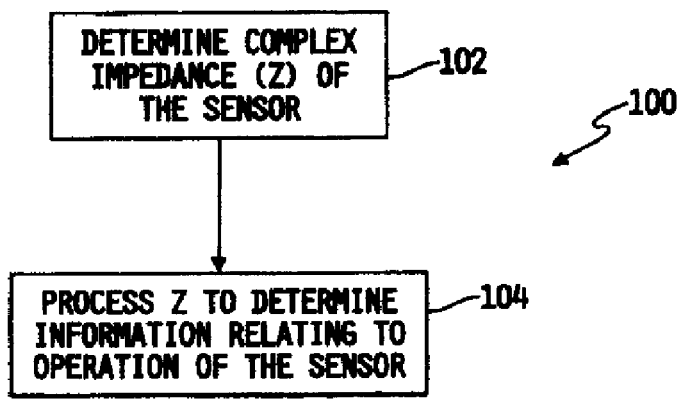
FIG. 4 is a flowchart of one illustrative embodiment of a process for operating the electrochemical analyte sensor of FIGS. 1 and 2.

Referring now to FIG. 4, a flow chart of one illustrative embodiment of a process 100 for operating the electrochemical analyte sensor 10 of FIGS. 1 and 2 is shown. The process 100 begins at step 102 where the electronic circuitry 64 is operable to determine the complex impedance, Z, of the sensor 10 using any one or more of the techniques described hereinabove. Thereafter at step 104, the electronic circuitry 64 is operable to process the complex impedance, Z, to determine information relating to operation of the sensor 10.

Figure 5:
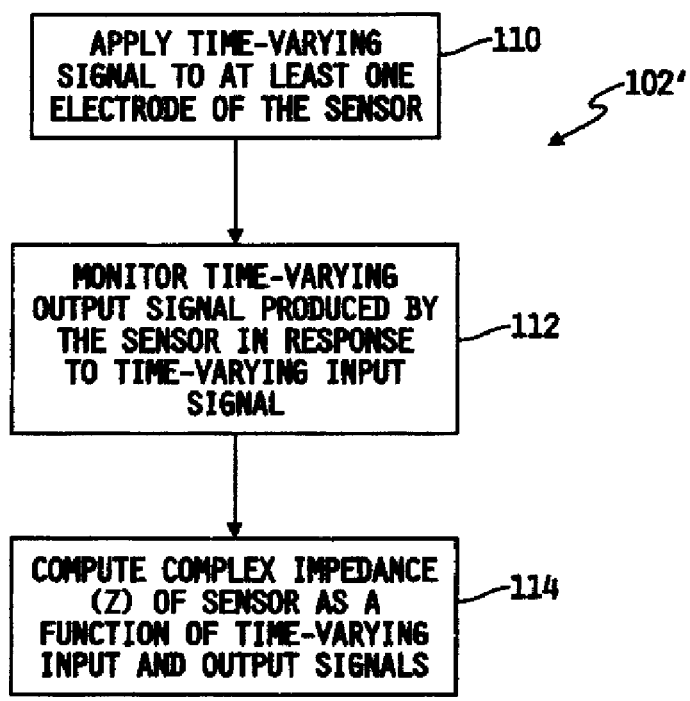
FIG. 5 is a flowchart of one illustrative embodiment of a process for carrying out the complex impedance determination step of the process of FIG. 4.

Referring now to FIG. 5, a flow chart of one illustrative embodiment of a process 102' for carrying out the complex impedance determination step 102 of the process of 100 of FIG. 4 is shown. The process 102' begins at step 110 where the electronic circuitry 64 is operable to apply a time-varying signal to at least one electrode of the sensor 10 as described hereinabove. Generally, the time-varying signal in this embodiment is a single or constant-frequency, time-varying voltage or current signal having any desired shape, e.g., sinusoidal, square-wave, etc., that may be applied to any one or more of the electrodes of the sensor 10.

In any case, the process 102' advances from step 110 to step 112 where the electronic circuitry 64 is operable to monitor the time-varying output signal produced by the sensor 10 in response to the time-varying input signal applied at step 110. Generally, the time-varying output signal may be a voltage or current signal, and may be measured by monitoring one or more of the electrodes of the sensor 10. In the specific embodiment illustrated in FIGS. 1-3, for example, step 112 is carried out by monitoring, via the impedance analyzer 70, the time-varying output voltage produced by the sensor 10, between the working and reference electrodes 24 and 28 respectively, in response to the time-varying input current signal applied by the AC current source 74 to the counter electrode 32. Following step 112, the process 102' advances to step 114 where the electronic circuitry 64 is operable to compute the complex impedance, Z, of the sensor 10 as a function of the time-varying input and output signals in a conventional manner and in accordance with known equations as described hereinabove. The time-varying input and output signals, as well as the complex impedance, Z, are generally time-varying vector quantities, and are typically expressed in the form of complex numbers. In one embodiment, for example, the complex numbers are provided in the form of polar coordinates each having a magnitude and associated phase. In some embodiments, the magnitude alone may be sufficient to determine a sensor characteristic of interest, and in other embodiments, the magnitude and phase are both used to determine one or more sensor characteristics of interest.

Figure 6:
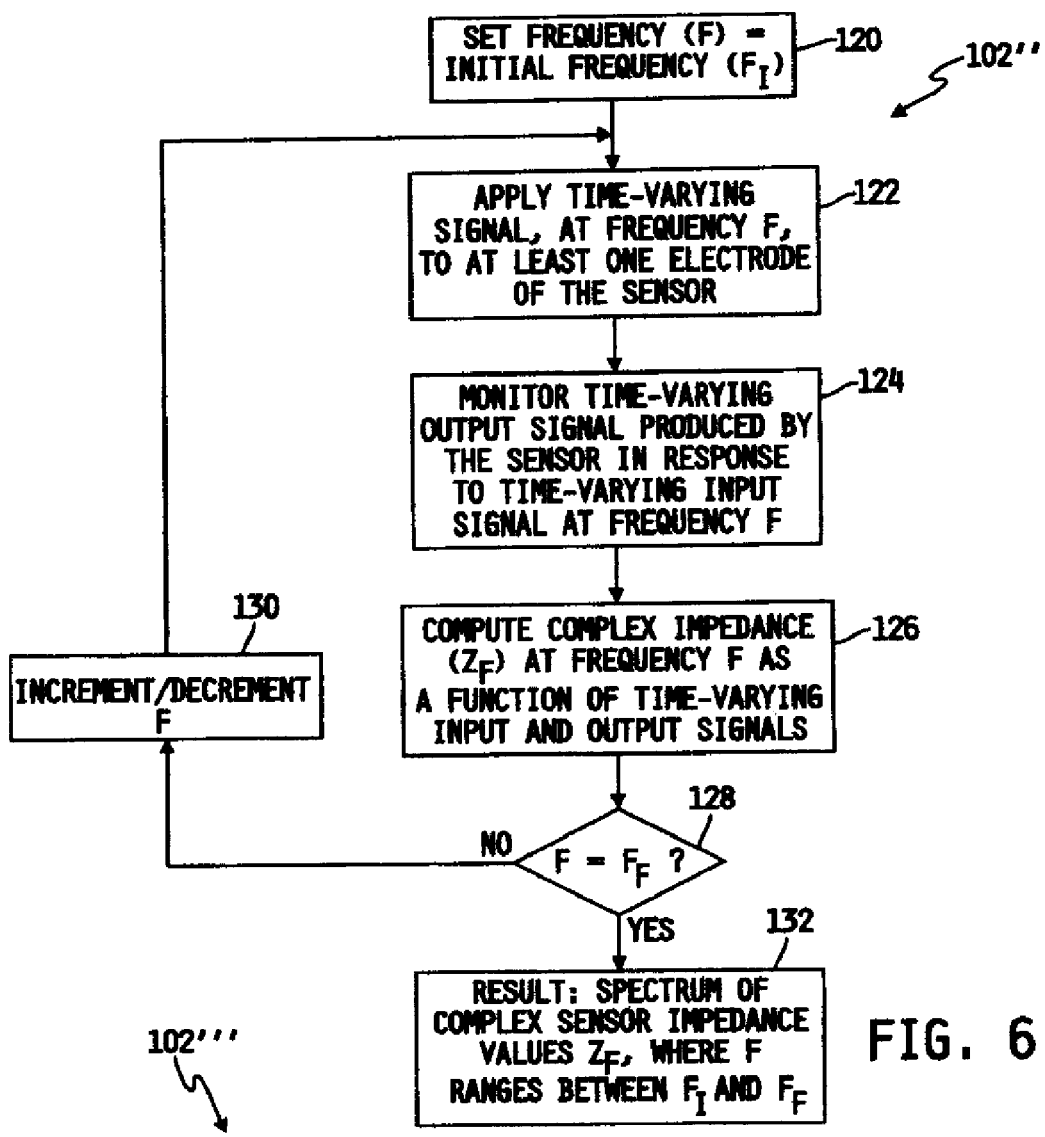
FIG. 6 is a flowchart of another illustrative embodiment of a process for carrying out the complex impedance determination step of the process of FIG. 4.

In some embodiments, it may be desirable to determine the complex impedance of the sensor 10 at multiple frequencies to thereby produce an impedance spectrum from which one or more properties or characteristics of the sensor 10 may be determined. Referring now to FIG. 6, a flow chart of another illustrative embodiment of a process 102" for carrying out the complex impedance determination step 102 of the process 100 of FIG. 4 is shown, wherein the process 102" is configured to determine a spectrum of complex sensor impedance values, $Z_F$, over a range of frequencies. The process 102" begins at step 120 where the electronic circuitry 64 is operable to set a frequency, F, of the time-varying input signal to an initial frequency value, $F_I$, so that the time-varying input signal initially varies in time at the frequency $F_I$. Thereafter at step 122, the electronic circuitry 64 is operable to apply the time-varying input signal, at the frequency F, to at least one electrode of the sensor 10. Generally, the time-varying signal in this embodiment is a time-varying voltage or current signal having any desired shape, e.g., sinusoidal, square-wave, etc., that may be applied to any one or more of the electrodes of the sensor 10.

From step 122, the process 102" advances to step 124 where the electronic circuitry 64 is operable to monitor a time-varying output signal, operating at the frequency, F, that is produced by the sensor 10 in response to the time-varying input signal operating at a frequency F. Generally, the time-varying output signal may be a voltage or current signal, and may be measured by monitoring one or more of the electrodes of the sensor 10.

From step 124, the process 102" advances to step 126 where the electronic circuitry 64 is operable to compute a complex impedance, $Z_F$, at the frequency F as a function of the time-varying input and output signals, both operating at the frequency F. Thereafter at step 128, the electronic circuitry is operable to determine whether the frequency F, of the time-varying input signal is equal to a final frequency, $F_F$. If not, the process 102" advances to step 130 where the frequency, F, is incremented or decremented to a next higher or lower incremental frequency value. Execution of the process 102" then loops back to step 122. If, at step 128, the electronic circuitry 64 determines that the frequency, F, of the time-varying signal source is equal to the final frequency, $F_F$, execution of the process 102" advances to step 132 where the frequency sweep of the time-varying signal source is complete and the result is a spectrum of complex sensor impedance values, $Z_F$, determined at sequential frequencies ranging between $F_I$ and $F_F$.

Figure 7:
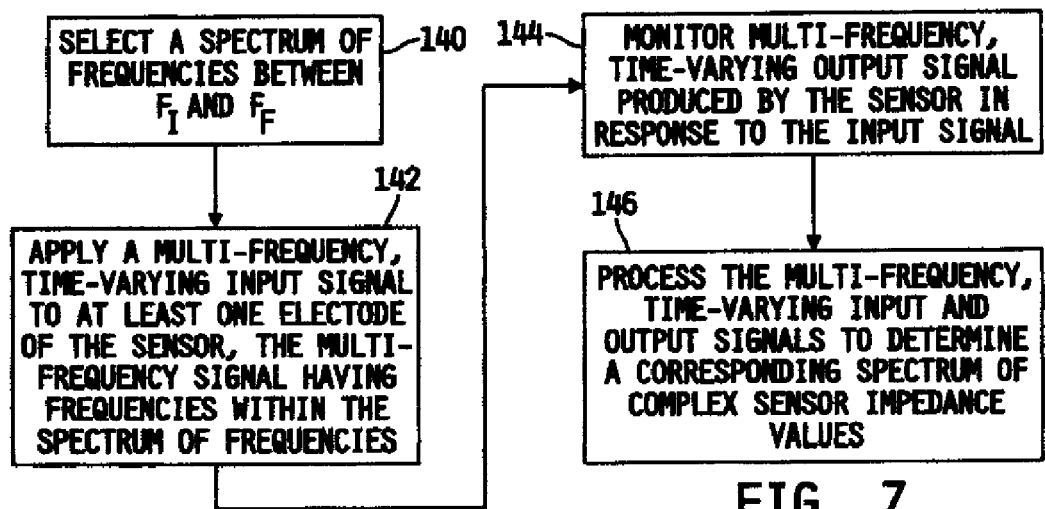
FIG. 7 is a flowchart of yet another illustrative embodiment of a process for carrying out the complex impedance determination step of the process of FIG. 4.

Referring now to FIG. 7, a flow chart of yet another illustrative embodiment of a process 102''' for carrying out the complex impedance determination step 102 of the process 100 of FIG. 4 as shown. Like the process 102', the process 102''' is configured to determine a spectrum of complex sensor impedance values, $Z_F$, at multiple frequencies. The process 102''' begins at step 140 where a spectrum of frequencies between an initial frequency, $F_I$, and a final frequency $F_F$ is selected. Thereafter at step 142, the electronic circuitry 64 is operable to apply a multiple-frequency, time-varying input signal to at least one electrode of the sensor, wherein the multi-frequency signal has or includes frequencies within the spectrum of frequencies between $F_I$ and $F_F$. Alternatively, the time-varying input signal may be made up of a sequence of multiple-frequency signals to allow determination of the complex impedance over different frequency ranges. Alternatively still, the time-varying input signal may be a complex mixture of frequencies such that the magnitude of the time-varying input signal remains small. Techniques for generating such input signals are known in the art.

Following step 142, the process 102''' advances to step 144 where the electronic circuitry 64 is operable to monitor the multiple-frequency, time-varying output signal produced by the sensor 10 in response to the multiple-frequency, time-varying input signal applied at step 142. Thereafter at step 146, the electronic circuitry 64 is operable to process the multiple-frequency, time-varying input and output signals to determine a corresponding spectrum of complex sensor impedance values, $Z_F$, that includes complex sensor impedance values at the multiple frequencies within the spectrum of frequencies between $F_I$ and $F_F$. In embodiments wherein the one or more time-varying input signals is/are provided in the form of a complex mixture of frequencies, analysis of the signal input and output information may be done at step 146 to determine the frequency components of the input and output signals using conventional signal processing techniques, examples of which include, but are not limited to, discrete Fourier Transform (DFT) analysis, Fast Fourier Transform (FFT) analysis or the like.

The complex sensor impedance information determined at step 102 of the process 100 of FIG. 4 is used at step 104 of the process 100 to determine information relating to the operating of the sensor 10. Such information may be or include, for example, but is not limited to, one or more different parameters relating to the operation of the sensor 10 in the environment containing the analyte, e.g., within the body 66 of the animal or human, one or more different characteristics of the sensor 10, a state of one or more different characteristics of the sensor 10, diagnostic information relating to the reliability of analyte measurement information produced by the sensor 10, or the like. One example of a parameter relating to the operation of the sensor 10 within the environment containing the analyte includes a measured values of one or more analytes that may be present within the body 66 in which the sensor 10 is inserted. Another example of a parameter relating to the operation of the sensor 10 in the environment containing the analyte includes an electrical conductivity of the environment containing the analyte, which may be determined as a function of the complex impedance in a known manner. Another example of a parameter relating to the operation of the sensor 10 includes a stability of the sensor 10 in the sense that, when stable, the information produced by the sensor is considered to be quality data that may be reliably used for computational purposes, and when not stable, the information produced by the sensor 10 is considered to be unreliable and should be disregarded and in any case not used for computational purposes. An example of a characteristic of the sensor includes a capacitance of the sensor 10, which may be determined as a function of the complex impedance in a known manner. An example of diagnostic information relating to the reliability of analyte measurement information produced by the sensor 10 includes comparing one or more complex sensor impedance values to one or more corresponding impedance thresholds and determining that an electrically conductive path associated with the sensor 10, e.g., a signal conductor, electrical connector or electrical trace, has failed if the one or more complex sensor impedance values is greater than the one or more corresponding complex impedance thresholds.

The state or operation of a characteristic of the sensor 10 may be determined by analyzing a spectrum of complex sensor impedance values, such as a spectrum determined over a range or multiple ranges of frequencies, using a conventional statistical procedure. Examples of such conventional statistical procedures include, but are not limited to, conventional regression techniques, principle component analysis (PCA) techniques, which may be used in a conventional manner to determine combinations of measured values that are relevant to one or more characteristics, and the like. Alternatively, the spectrum of complex sensor impedance values may be analyzed to determine the state of a characteristic or of operation of the sensor 10 by using a conventional equivalent circuit technique wherein the complex sensor impedance spectrum is fit to an impedance spectrum of an equivalent circuit model by adjusting values of the circuit model components until a best fit is achieved. The resulting component values may then be representative of characteristics or operation of the sensor or sensor circuit, examples of which may include, but are not limited to, the concentration of one or more analytes to which the sensor is exposed, resistance of a solution or environment in which the sensor is immersed or exposed to, electrode surface area, membrane permeability, etc. Alternatively, the circuit component values may be used as inputs to a statistical procedure, e.g., regression, PCA or the like, to determine one or more specific sensor characteristics.

Figure 8A:
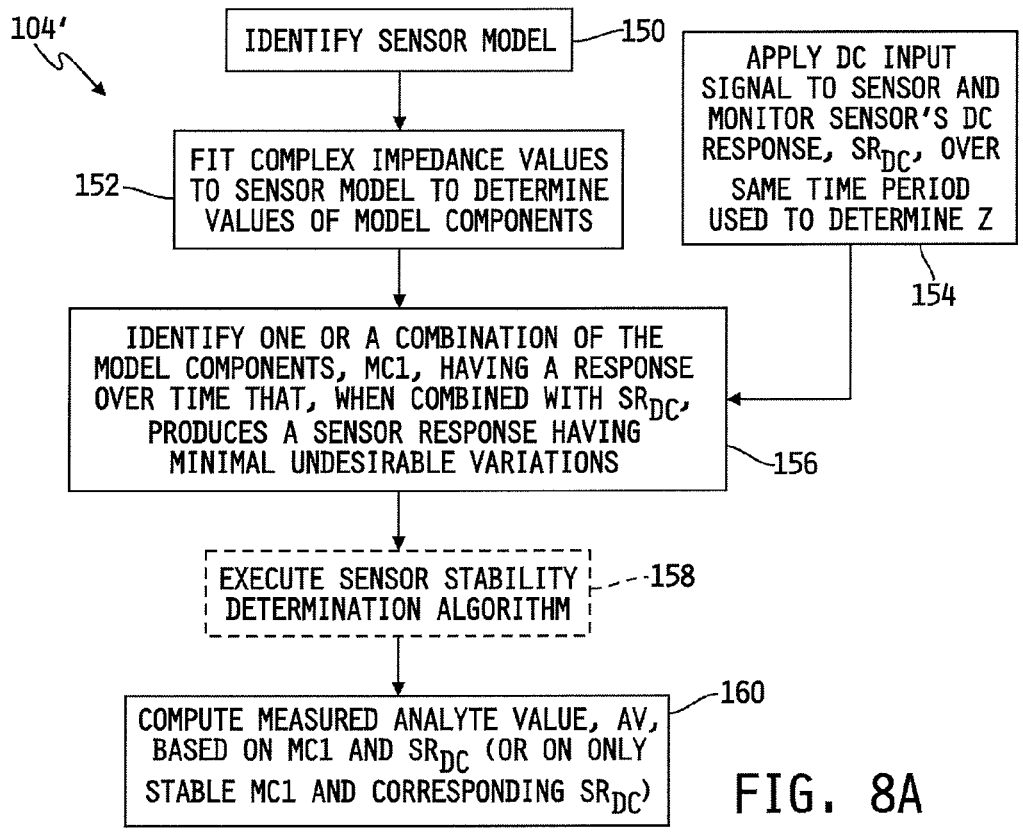
FIG. 8A is a flowchart of one illustrative embodiment of a process for carrying out the last step of the process of FIG. 4

Referring now to FIG. 8A, a flow chart of one illustrative embodiment of a process 104' is shown for carrying out step 104 of the process 100 of FIG. 4, i.e., processing the impedance information, Z, to determine information relating to operation of the sensor 10. The process 104' begins at step 150 where a sensor model is identified. Illustratively, as will be described in greater detail in the examples that follow, the sensor model may be a conventional equivalent circuit model. Alternatively or additionally, the sensor model may be or include one or more other conventional models for representing or characterizing the sensor 10 over one or more frequency ranges of interest. Following step 150, the process 104' advances to step 152 where the complex impedance values resulting from step 102 of the process 100 are fit to the sensor model identified at step 150 of the process 104', using one or more conventional data fitting techniques, to determine values of the various model components.

The process 104' includes a step 154 that is executed prior to or concurrently with steps 150 and 152. Alternatively, step 154 may be included within step 102 of the process 100. In any case, at step 154 a DC input signal is applied to the sensor 10 in any manner described herein, and the sensor's resulting DC response, $SR_{DC}$, is monitored and sampled over the same time period used to determine the complex impedance, Z. In the illustrated embodiment, steps 152 and 154 advance to step 156 where one or a functional combination of the model components, MC1, is identified that has a response over time that, when combined with the DC response, $SR_{DC}$, of the sensor 10, produces a sensor response that has minimal undesirable variations in the response magnitude over time. As used herein, the term "minimal" should be understood to mean that the undesirable variations in the response magnitude over time are minimized to a tolerable level, or are at least reduced as compared with variations, over time, in the magnitude of the DC response alone. The combination of the one or more model components, MC1, with the DC response, $SR_{DC}$, may be any mathematical function including, for example, a simple mathematical relationship such as a product, ratio, sum or difference of MC1 and $SR_{DC}$, or a more complex linear, non-linear, continuous, non-continuous and/or piecewise continuous function of MC and $SR_{DC}$. The one or more model components, MC1, may be or include, for example, a single model component or any mathematical function including, for example, a simple mathematical relationship such as a product, ratio, sum or difference of two or more model components, or a more complex linear, non-linear, continuous, non-continuous and/or piecewise continuous function of two or more model components. The undesirable variations sought to be minimized within a tolerable level, or at least reduced as just described, may be or include, for example, but are not limited to, sensor sensitivity drift over time, sensor offset drift over time, sensor signal sensitivity and/or offset variations during an initial break-in period of the sensor 10, anomalies present in the sensor signal and/or in sampled sensor signal data, and the like.

Figure 9:
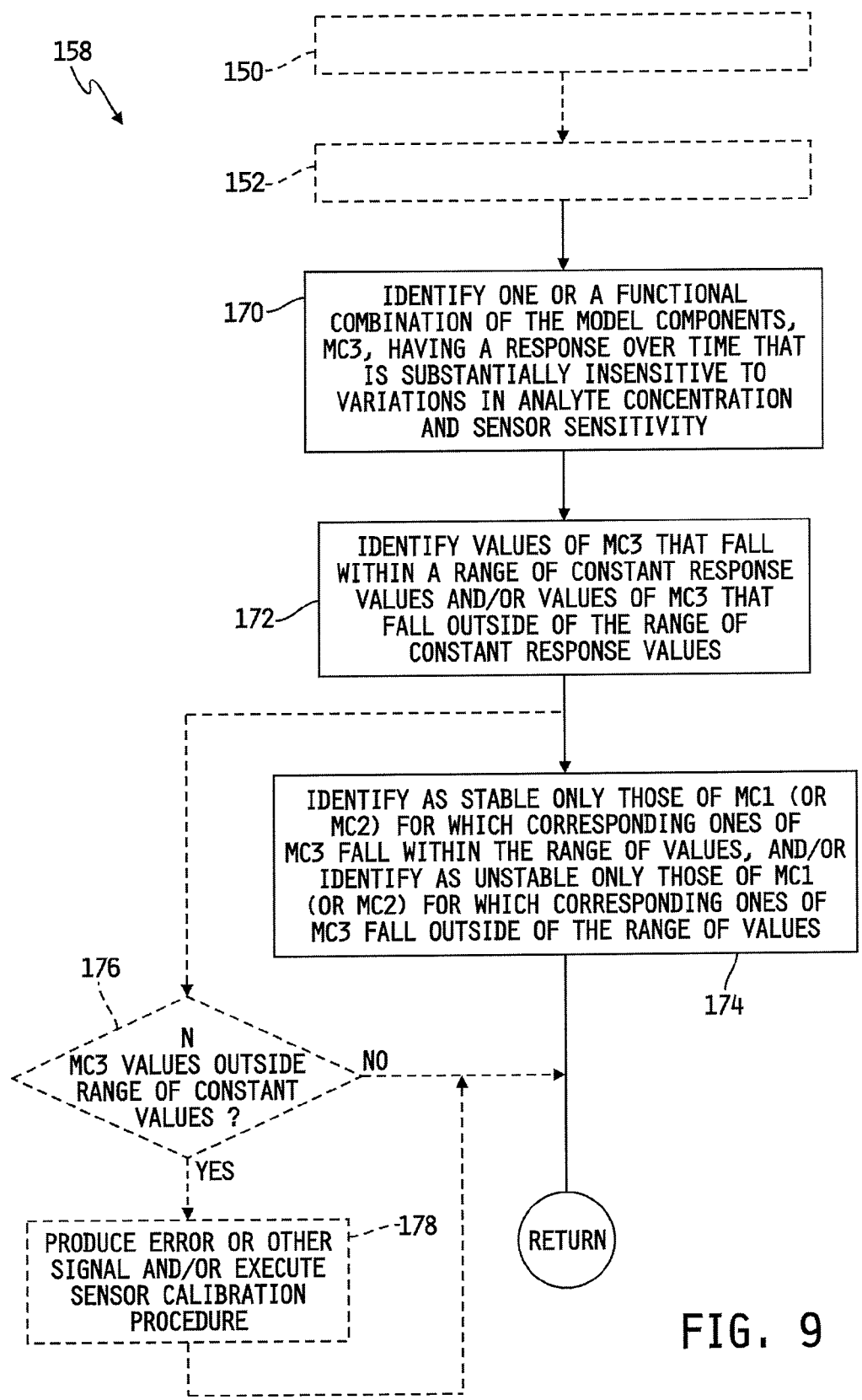
FIG. 9 is a flowchart of one illustrative embodiment of a process for determining the stability of a continuous analyte sensor.

The process 104' may include an optional step 158, as shown by dashed-line representation in FIG. 8A, and in such embodiments, step 156 advances to step 158. If included in the process 104', a sensor stability determination algorithm is executed at step 158. Referring to FIG. 9, one illustrative embodiment of the sensor stability determination algorithm 158 is shown. In the illustrated embodiment, the algorithm 158 begins at step 170 where one or a functional combination of the model components, MC3, is identified that has a response over time that is substantially insensitive to variations in analyte concentration and sensor sensitivity. A functional combination of the one or more model components, MCs, may be any mathematical function including, for example, a simple mathematical relationship such as a product, ratio, sum or difference of two or more model components, or a more complex linear, non-linear, continuous, non-continuous and/or piecewise continuous function of two or more model components.

The algorithm 158 advances from step 170 to step 172 where values of MC3 that fall within a range of constant response values, and/or values of MC3 that fall outside of the range of constant response values, are identified. In one embodiment, step 172 is executed by monitoring a rate of change of MC3 over time, and determining that MC3 components fall within the range of constant response values as long as the rate of change of MC3 is less than a predetermined rate of change value. The MC3 components that fall outside of the range of constant response values are those that have a rate of change that is greater than the predetermined rate of change value. Alternatively, step 172 may be executed in this embodiment by determining that MC3 components fall outside the range of constant response values if the rate of change of MC3 is greater than the predetermined rate of change value, and those that do not meet this criterion are deemed to fall inside of this range. In an alternate embodiment, step 172 may be executed by monitoring the magnitudes of individual MC3 values, and determining that each MC3 component value falls within the range of constant response values if its magnitude is less than or equal to a predetermined magnitude value. MC3 values that do not meet this criterion fall outside of this range. Alternatively, step 172 may be executed in this embodiment by determining that each MC3 component value falls outside of the range of constant response values if its magnitude is greater than the predetermined magnitude value, and MC3 values that do not meet this criterion fall within this range. Those skilled in the art will recognize other conventional techniques for identifying the MC3 values that fall within, and/or outside of, the range of constant response values, and any such other conventional techniques are contemplated by this disclosure.

The algorithm 158 advances from step 172 to step 174 where only the values of MC1 (or MC2 as in the case of FIG. 8B) for which values of corresponding ones of MC3 fall within the range of constant response values are identified as being stable response values, and/or where only the values of MC1 (or MC2) for which values of corresponding ones of MC3 fall outside of the range of constant response values are identified as being unstable response values. Illustratively, the stable values of MC1 (and/or MC2) may be identified at step 174 so that only these values may be subsequently used to determine corresponding measured analyte values. The unstable values of MC1 (and/or MC2), in this embodiment, are considered to be unsuitable for the purpose of determining measured analyte values. Alternatively or additionally, the unstable values of MC1 (and/or MC2) may be identified at step 174 so that these values may be processed in accordance with a sensor diagnostics process.

FIG. 9 further illustrates a number of dashed-line steps, and one or more such steps may be included in the algorithm 158 in one or more alternative embodiments thereof. For example, steps 150 and 152 of the process 104' may be included in the algorithm 158 in embodiments in which the algorithm 158 may be a stand-alone algorithm that may be executed independently of step 104 of the process 100 to determine whether an output response of the sensor 10 is stable. In one embodiment in which the algorithm 158 includes step 150 and 152, and is a stand-alone algorithm that may be executed independently of step 104 of the process 100 to determine whether an output response of the sensor 10 is stable, step 174 may be modified to identify as stable only sensor output response samples for which the values of corresponding ones of the one or a functional combination of the model components fall within a range of response values. Such modification of step 174 would be a mechanical step for a skilled artisan.

Alternatively or additionally, steps 176 and 178 may be included in embodiments in which the algorithm 158 is used to monitor the MC3 components and to produce an error signal, e.g., error flag, or other signal when one or more MC3 components are found to be outside of the range of constant response values, i.e., found to be unstable. In this embodiment, step 172 may alternatively advance to step 176 where it is determined whether some number, e.g., one or more, of the MC3 values fall outside of the range of constant response values. If so, the algorithm 158 advances to step 178 where the error signal or other signal is produced. If not, no error or signal is produced. As one alternative to producing an error signal or other signal, step 178 may alternatively advance to a sensor calibration or recalibration process. In any case, steps 176 and 178 may be included in lieu of, or in addition to, step 174, and may be included in embodiments that include steps 150 and 152 and/or in embodiments that do not include steps 150 and 152.

Referring again to FIG. 8A, step 156 advances to step 160, in embodiments that do not include step 158, where measured analyte values, AV, are computed based on the combination of MC1 and $SR_{DC}$ as described above. In embodiments that include step 158, only the MC1 values that were identified by the algorithm 158 as being stable are used, along with corresponding $SR_{DC}$ values, in the computation of the measured analyte values. In any case, step 160 may be executed using any one or more conventional techniques for solving equations and/or fitting data. Examples include, but are not limited to, solving the function of MC1 and $SR_{DC}$ using conventional algebra, geometry and/or calculus in any N-dimensional coordinate system, wherein N may be any positive integer, and using any conventional statistical or other data fitting techniques to fit the complex impedance data to the function of MC1 and $SR_{DC}$, such as principle component analysis, empirical analysis or the like.

Figure 8B:
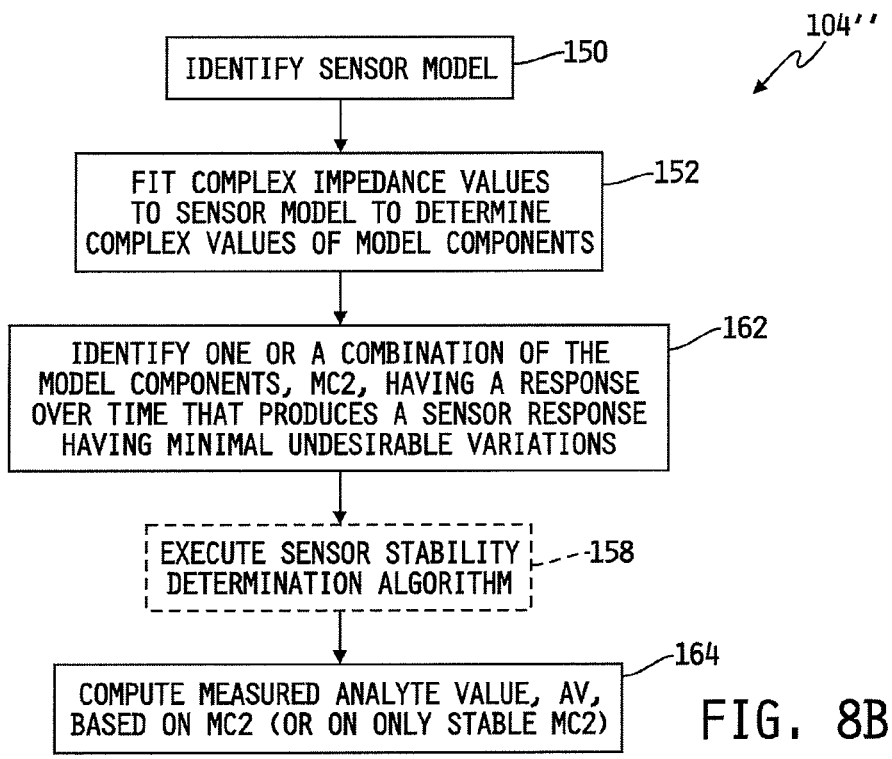
FIG. 8B is a flowchart of another illustrative embodiment of a process for carrying out the last step of the process of FIG. 4.

Referring now to FIG. 8B, a flow chart of another illustrative embodiment of a process 104" is shown for carrying out step 104 of the process 100 of FIG. 4, i.e., processing the impedance information, Z, to determine information relating to operation of the sensor 10. The process 104" includes a number of steps in common with the process 104' just described, such as steps 150 and 152, and the optional step 158. In the illustrated embodiment, step 152 of the process 104" advances to step 162 where one or a functional combination of the model components, MC2, are identified that has a response over time that produces a sensor response that has minimal undesirable variations in the response magnitude over time, as has been described above. The one or more model components, MC2, may be or include, for example, a single model component or any mathematical function including, for example, a simple mathematical relationship such as a product, ratio, sum or difference of two or more model components, or a more complex linear, non-linear, continuous, non-continuous and/or piecewise continuous function of two or more model components. The undesirable variations sought to be minimized may be or include, for example, but are not limited to, sensor sensitivity drift over time, sensor offset drift over time, sensor signal sensitivity and/or offset variations during an initial break-in period of the sensor 10, anomalies present in the sensor signal and/or in sampled sensor signal data, and the like.

The process 104" may, in some embodiments, include the sensor stability determination step 158 that was described in detail hereinabove. Step 162 advances to step 164, in embodiments that do not include step 158, where measured analyte values, AV, are computed based on MC2 as described above. In embodiments that include step 158, only those MC2 values that were identified as being stable are used to compute the measured analyte values. In any case, step 164 may be executed using the MC2 values directly in the computation of analyte concentration values according to known relationships, or by using any one or more conventional techniques for fitting data. Examples of conventional data fitting techniques include, but are not limited to, any conventional statistical or other data fitting techniques such as principle component analysis, empirical analysis or the like.

The following examples were conducted in-vitro using the continuous analyte sensor 10 electrically connected to the electronic circuitry 64 via the electrical connector 50 as illustrated in FIGS. 1-3. These examples are provided to illustrate one or more concepts of this disclosure, and should not be considered to be limiting in any way.

Example 1

In this example, the sensor 10' illustrated and described with respect to FIG. 1B was placed in a conventional flow cell that was fluidly coupled to a conventional 2-channel high performance liquid chromatography pump (HPLC). The pump was controlled to produce the glucose concentration (mM/L) vs. time profile 200 illustrated in FIG. 10 (over approximately a two and one-half day period). The potentiostat 70 was configured in a conventional manner to apply a constant (DC) voltage of approximately 350 mV between the working electrode 24 and the reference electrode 28. The DC voltage was then used in an internal feedback path to modulate a time-varying (AC) current applied to the counter electrode 32 at intervals of approximately every 16-17 minutes, which resulted in a time-varying (AC) voltage of approximately 5 mV rms between the working electrode 24 and the reference electrode 28 at intervals of approximately every 16-17 minutes. The frequency of the time-varying voltage was swept from 100,000 Hz to 0.01 Hz with a step size of 5 equally-spaced frequency divisions per decade on a log scale to produce 36 different frequency values per frequency sweep. The current through the working electrode 24 was monitored as the output of the sensor 10'. DC output current measurements were taken by passing the output current values through a low-pass filter algorithm stored in the memory 74 and executed by the processor 72, and AC output current measurements were taken by passing the output current values through a high-pass filter algorithm stored in the memory 74 and executed by the processor 72. A complex impedance vector, Z, was determined at each frequency sweep as a function of a vector, I, of the AC output current measurements and a vector, E, of corresponding AC input voltage values, e.g., $Z=E/I$, wherein each of the vectors Z, I and E contain 36 different impedance, current and voltage values respectively.

Figure 10:
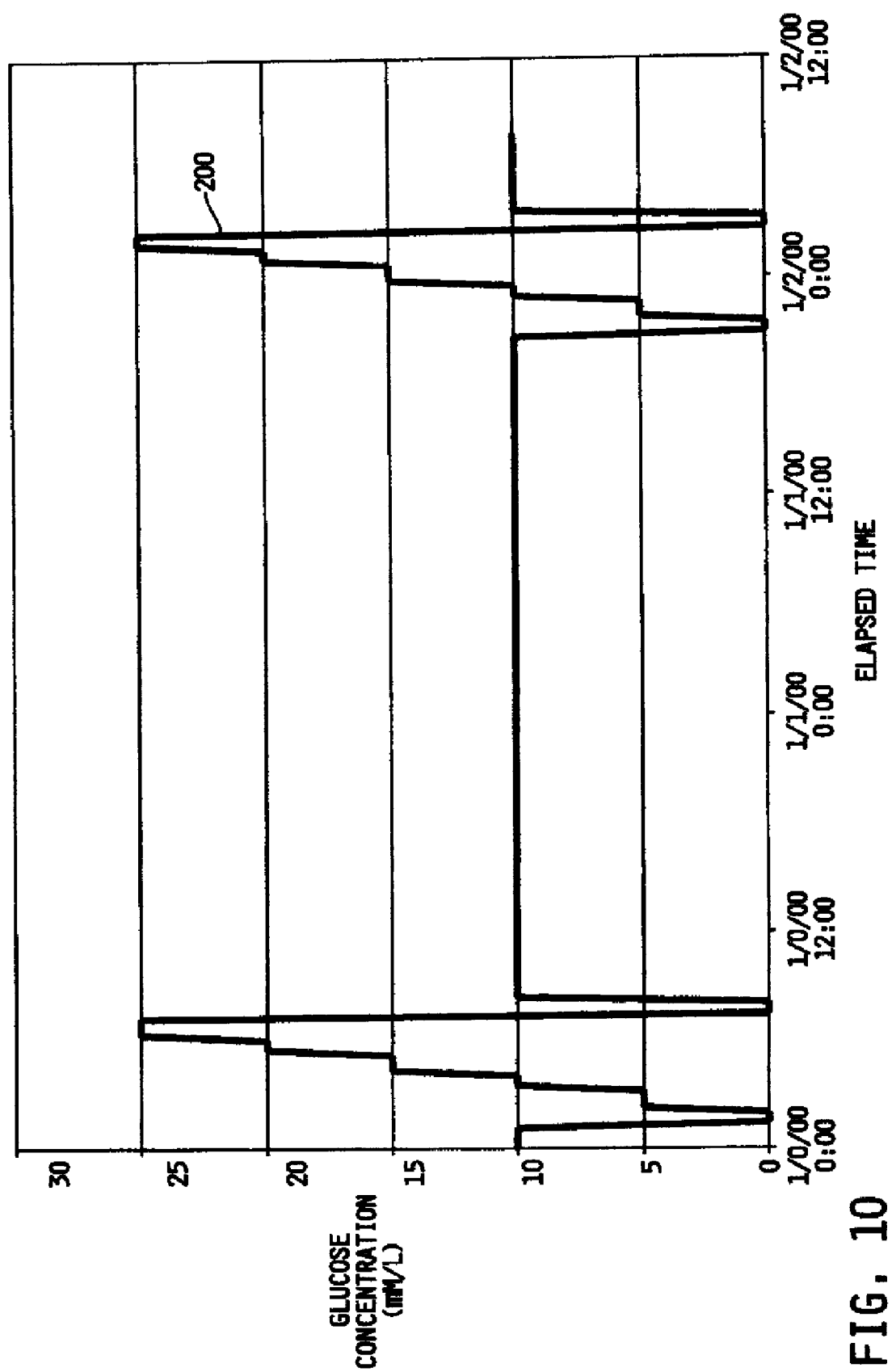
FIG. 10 is a plot of glucose concentration vs. time illustrating a glucose profile to which the continuous analyte sensor was exposed in a first experimental set up.
Figure 11:
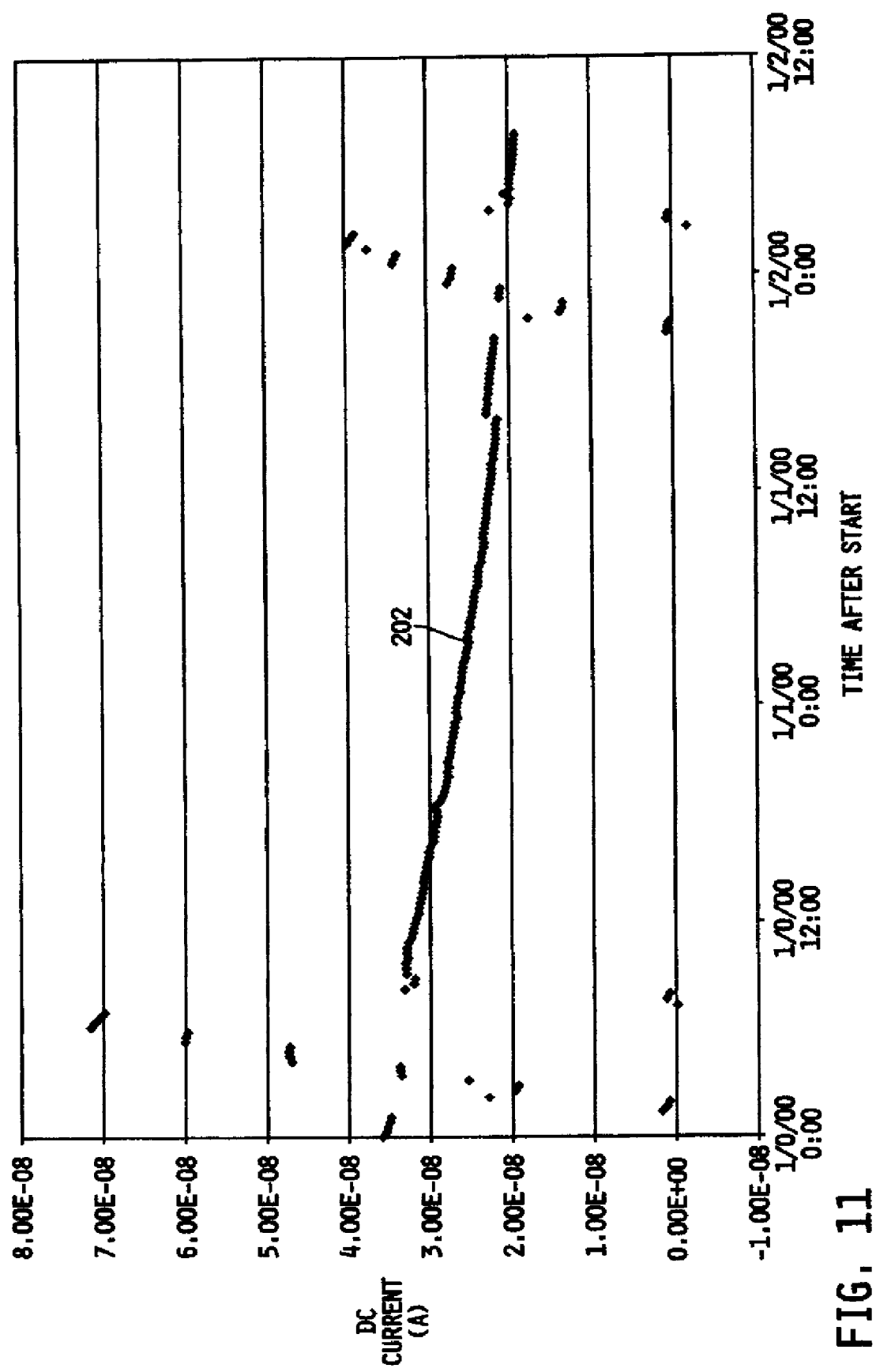
FIG. 11 is a plot of the DC current response of the continuous analyte sensor in the first experimental set up.

FIG. 11 is a plot of the DC current 202 produced by the sensor 10' vs. time using the same time scale as FIG. 10. The DC current 202 produced by the continuous analyte sensor 10' is illustrative of the drift typically observed in the DC response over time of a conventional continuous analyte sensor.

Figure 12:
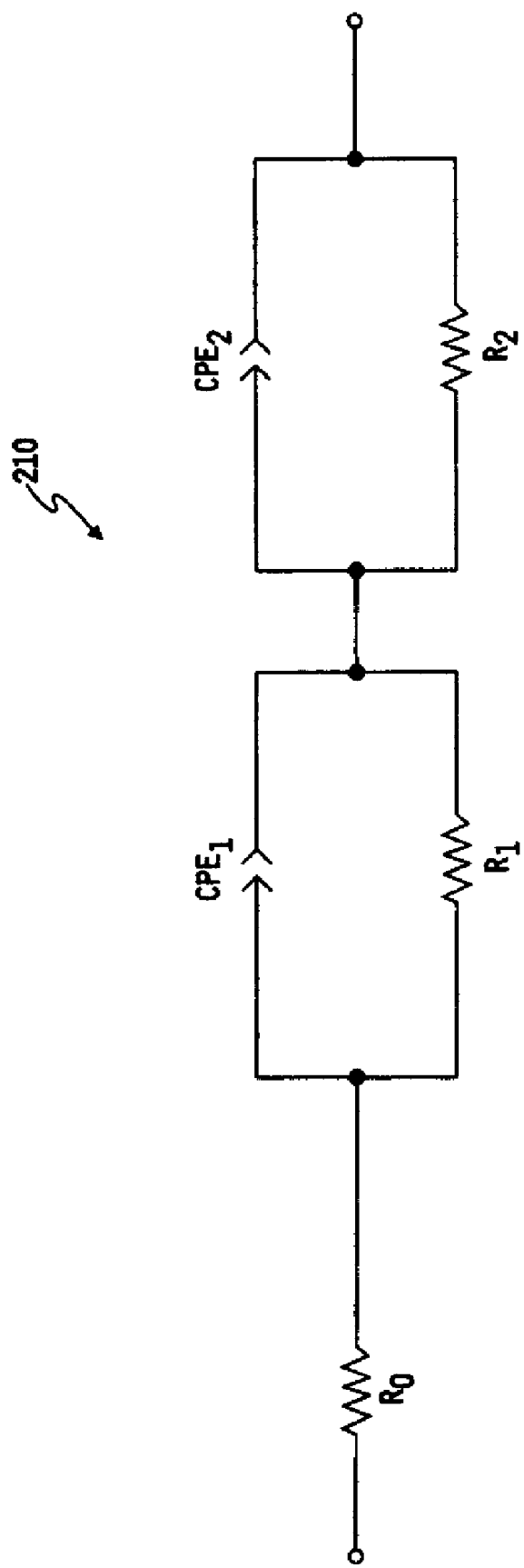
FIG. 12 is a diagram of an equivalent circuit to which the AC response of the sensor was fitted in the first experimental set up.

Referring now to FIG. 12, an equivalent circuit model 210 of the sensor 10' is shown. The model 210 consists of a resistor, $R_O$, in series with the parallel combination of a constant phase element, CPE1, and another resistor, $R_1$, and also with the parallel combination of another constant phase element, CPE2, and another resistor, $R_2$. The constant phase elements, CPE1 and CPE2 are capacitive elements each having a constant phase of between 0 and 90 degrees. The equivalent circuit model 210 of the sensor 10' is defined mathematically by the following equations:

$$Z=R_O+[(Z_1 *R_1)/(Z_1+R_1)]+[(Z_2 *R_2)/(Z_2+R_2)] \quad (1),$$

$$Z_1=1/[T_1 *(jw)^{P1}] \quad (2),$$

$$Z_2=1/[T_2 *(jw)^{P2}] \quad (3),$$

$$P1=(P2)/2 \quad (4).$$

Figure 13:
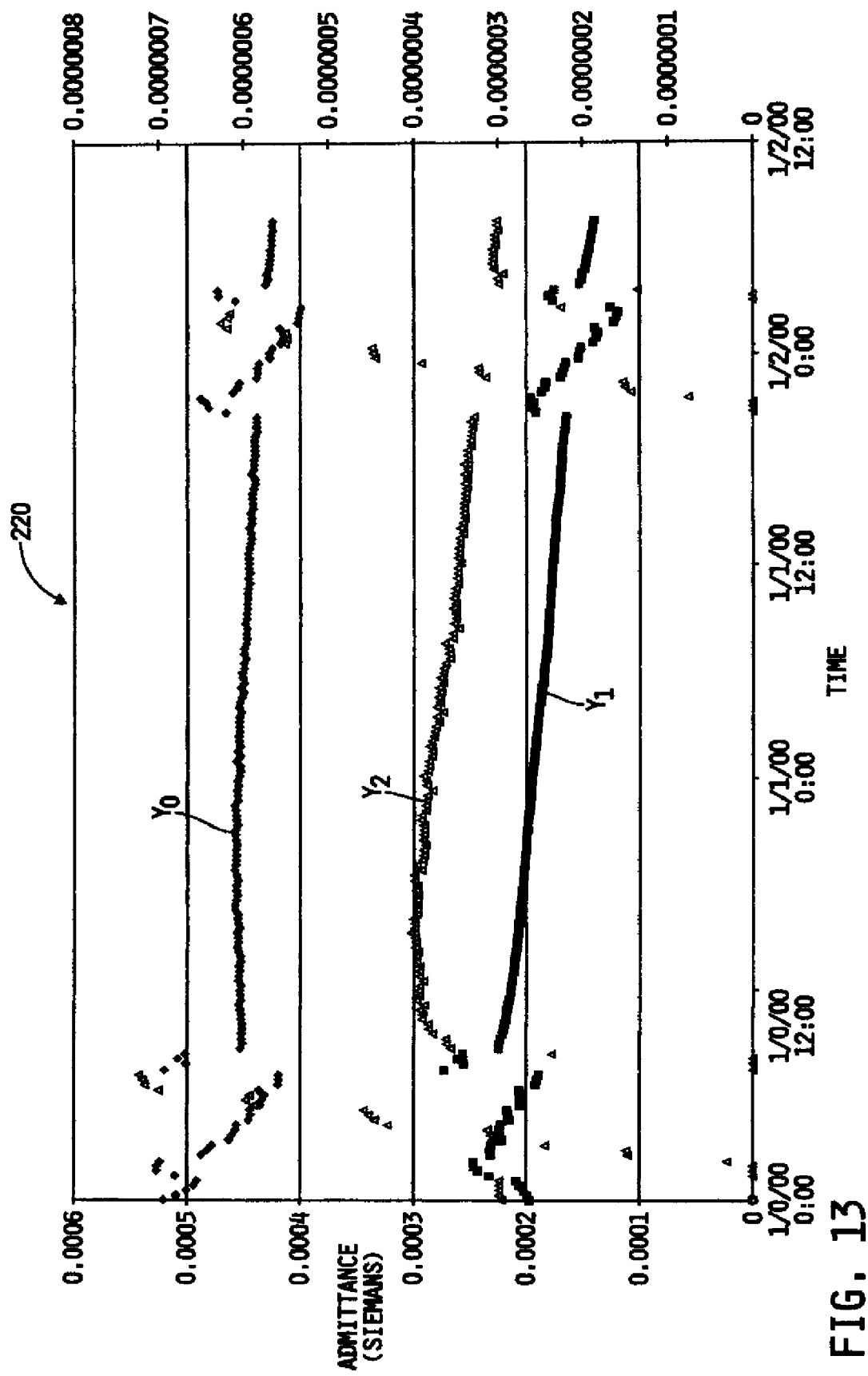
FIG. 13 is a plot of the admittance values vs. time of the resistor components of the equivalent circuit of FIG. 12.
Figure 14:
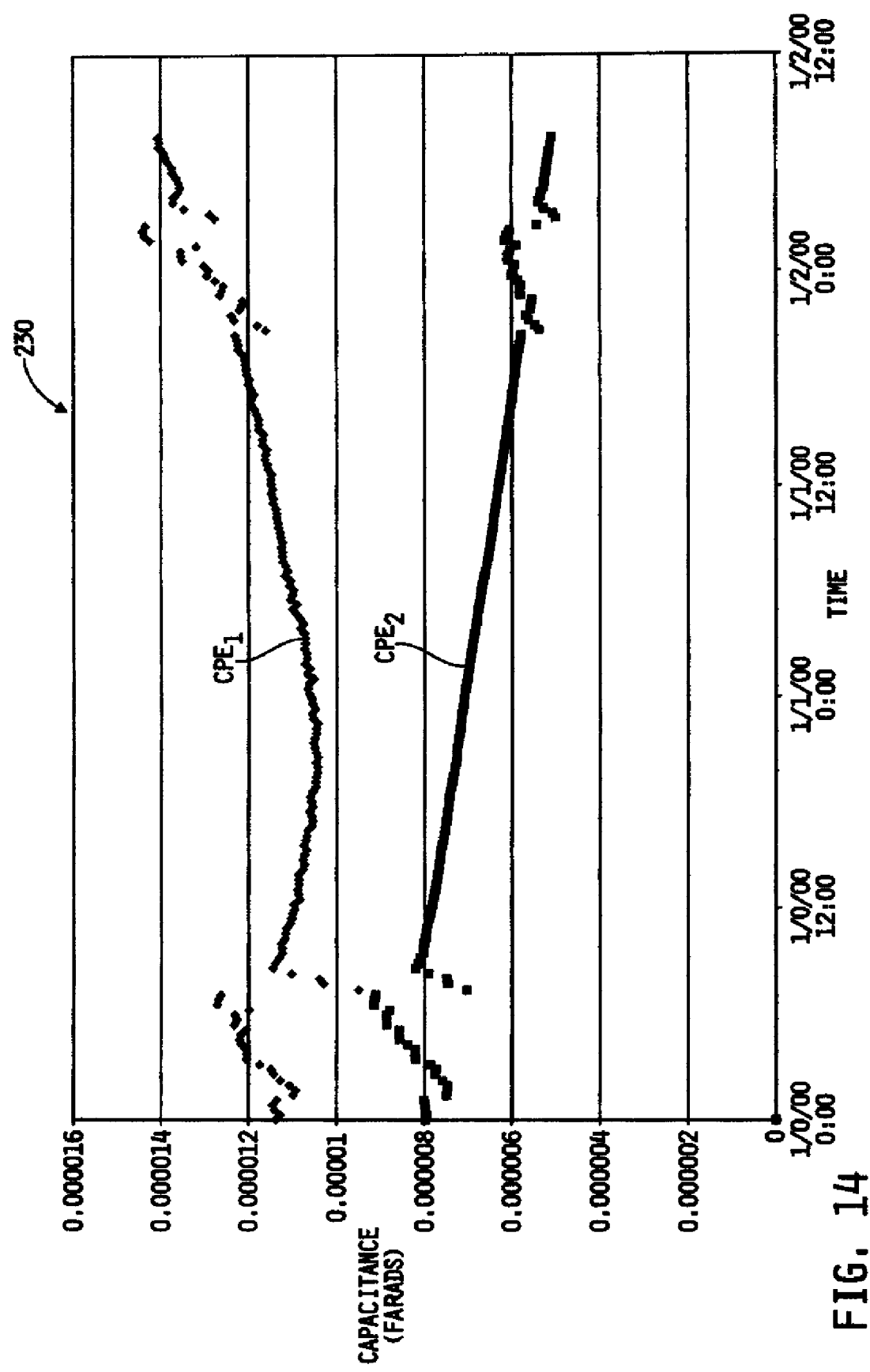
FIG. 14 is a plot of the capacitance values vs. time of the constant phase components of the equivalent circuit of FIG. 12.

The parameters $R_0$, $R_1$, $R_2$, $T_1$, $T_2$, P1 and P2 are model parameters, where $T_1$ and $T_2$ are in units of siemens or 1/ohms, and P1 and P2 are dimensionless. The sensor impedance data produced by the sensor 10' in response to each application of the AC voltage over the range of frequencies was fit to the equations (1)-(4). More specifically, for each AC voltage application, sensor impedance data (magnitude and phase) over 31 frequencies ranging from 10,000 Hz to 0.01 Hz was fit to a single set of equivalent circuit component values using conventional non-linear regression techniques. For the time duration indicated in FIGS. 10 and 11, e.g., approximately 2½ days, the AC voltage was applied approximately 200 times, thus resulting in approximately 200 equivalent circuits each having a unique set of component values. A plot 220 of the resulting admittance values, $Y_O$, $Y_1$ and $Y_2$, corresponding to $1/R_O$, $1/R_1$ and $1/R_2$ respectively, is shown in FIG. 13, and a plot 230 of the resulting capacitance values CPE1 and CPE2 is shown in FIG. 14. The total complex impedance, Z, of the sensor 10 is represented by equation (1).

Figure 15:
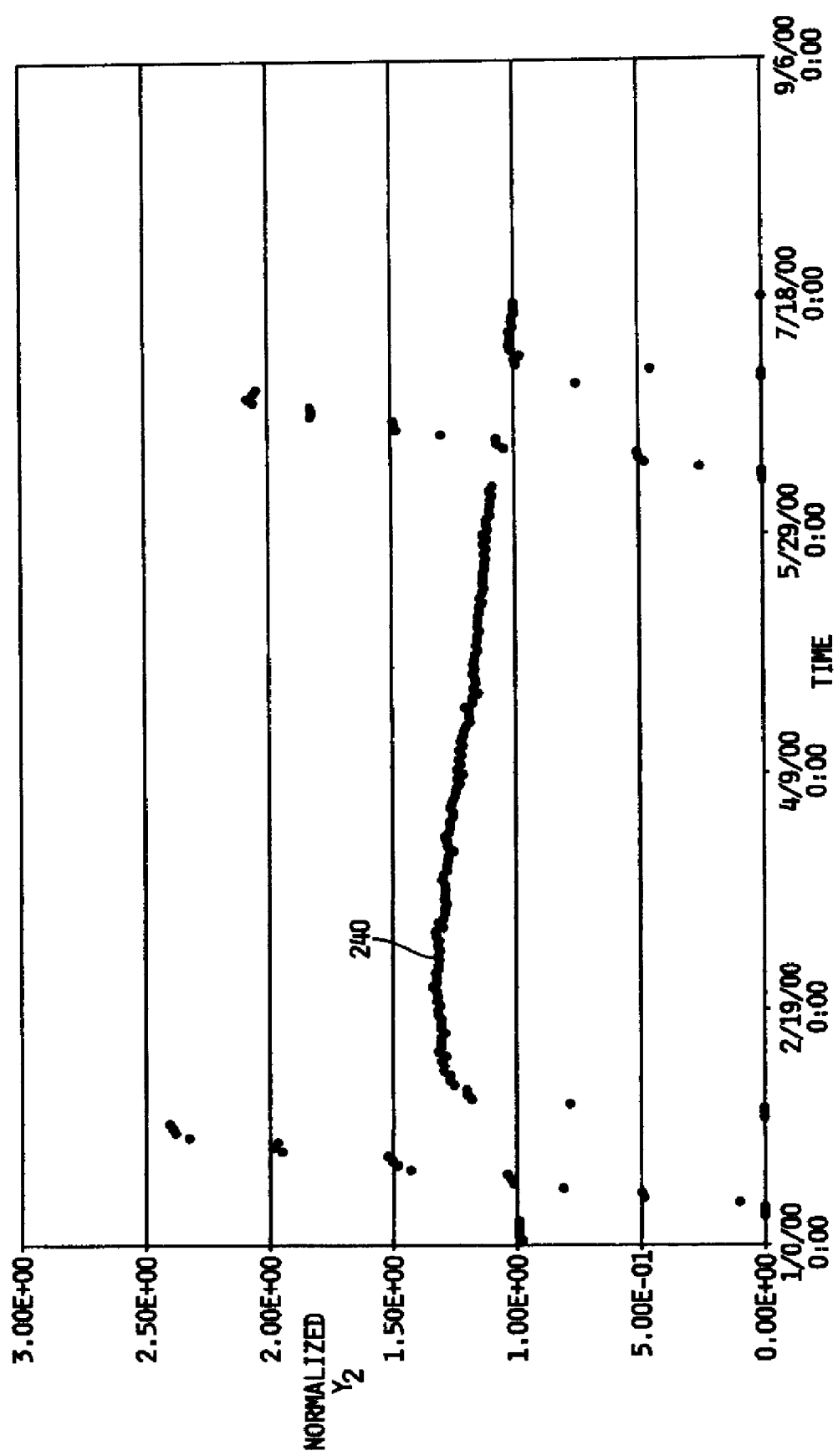
FIG. 15 is a plot of normalized admittance vs. time of the resistor $R_2$ of the equivalent circuit of FIG. 12.
Figure 16:
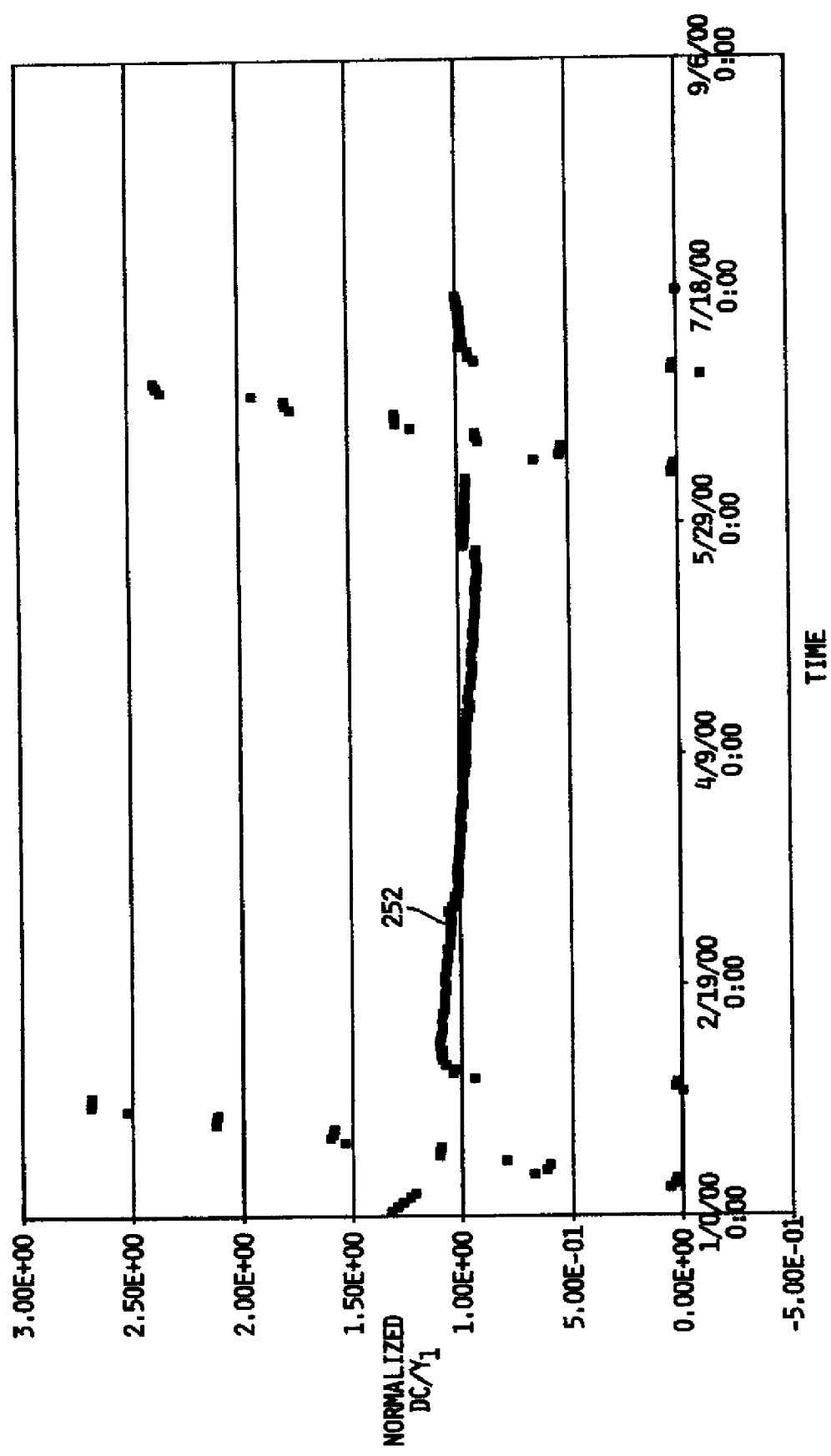
FIG. 16 is a plot of a normalized ratio of the DC sensor response and an admittance of the resistor $R_1$ of the equivalent circuit of FIG. 12.
Figure 17:
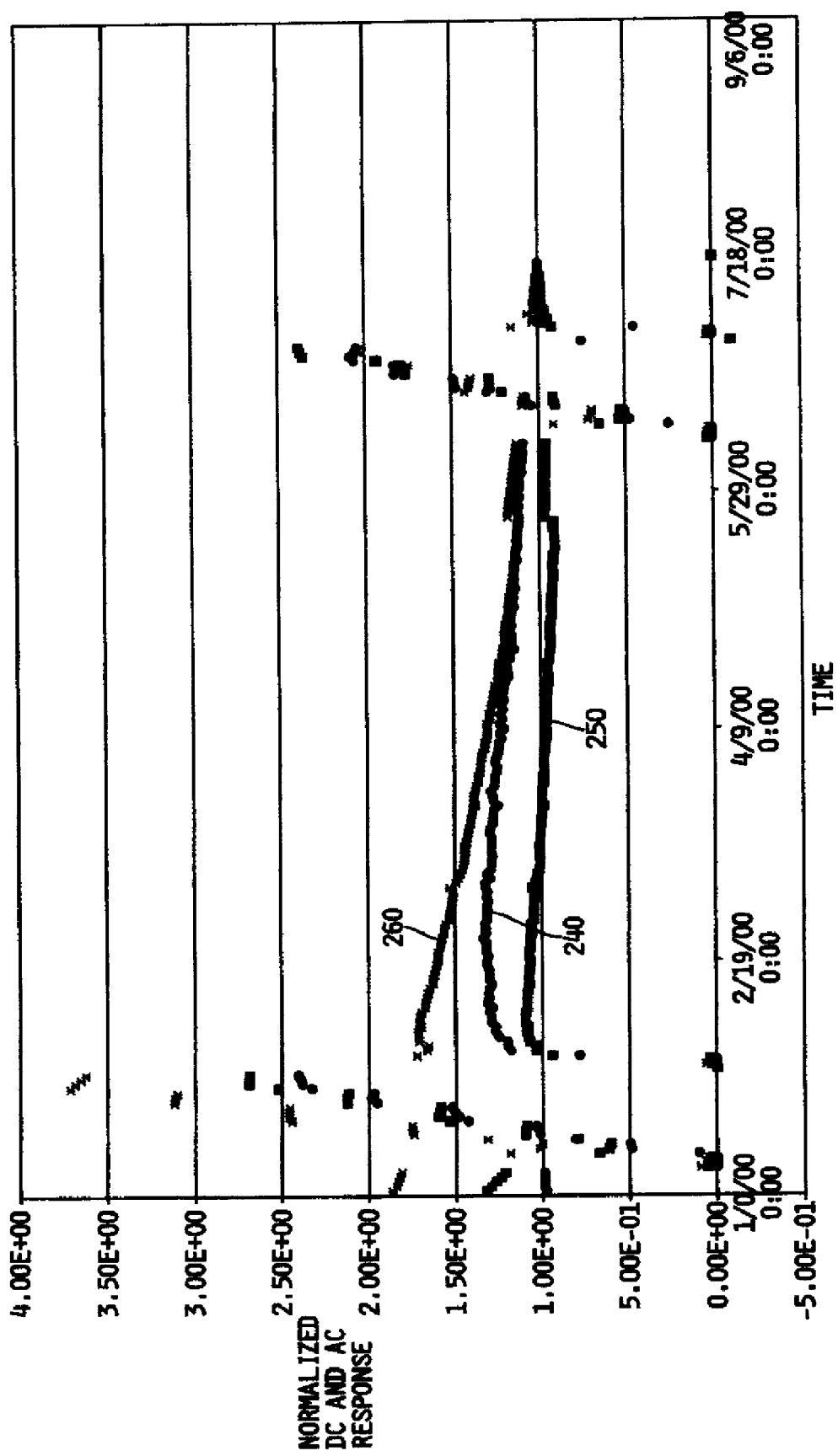
FIG. 17 is a plot comparing the normalized DC response of the sensor, the normalized admittance of the resistor $R_2$ and the normalized ratio of the DC sensor response and the admittance of the resistor $R_1$ vs. time.

FIG. 15 is a plot 240 of the admittance value, $Y_2$, vs. time and FIG. 16, is a plot 250 of a ratio of the DC sensor response and the admittance value, $Y_1$, e.g., $DC/Y_1$, vs. time, wherein $Y_2$ 240 and $DC/Y_1$ 250 have each been normalized to have a final or last value of 1. FIG. 17 is a plot comparing a normalized DC response 260 of the sensor 10 with the normalized admittance, $Y_2$, 240 and the normalized ratio of $DC/Y_1$ 250 vs. time. As compared with the normalized DC response 260 of the sensor 10', the normalized admittance value, $Y_2$, 240 exhibits less drift over time. Accordingly, the AC response 240 of one of the impedance components of the equivalent circuit model of the sensor 10', e.g., $Y_2$, may be used alone to provide more accurate sensor data over time than the DC response alone. As compared with the normalized DC response 260 of the sensor 10' and the normalized admittance value, $Y_2$, 240, the ratio $DC/Y_1$ 250 exhibits the least amount of drift over time. Accordingly, the ratio of the DC response 260 and one of the impedance components of the equivalent circuit model of the sensor 10', e.g., $DC/Y_1$ 250, may alternatively be used. Thus, by using the AC response of one of the impedance components alone, e.g., $Y_2$ 240, or correcting the conventional time-drifting DC response 260 of a continuous analyte sensor 10' with a suitable time-varying (AC) impedance component, e.g., $Y_1$, of the equivalent circuit model of the sensor 10', the resulting analyte measurements will be substantially more constant over time than the DC response 202 (FIG. 11) alone. It will be appreciated that this disclosure contemplates other embodiments wherein the DC response 260 of the sensor 10' may be compensated by a mathematical function of two or more impedance components of the equivalent circuit model, or that a mathematical function of two or more impedance components of the equivalent circuit model of the sensor 10' may be used alone to provide sensor data over time from which analyte concentration is determined, wherein such compensation provides for more constant analyte information over time than with the DC response alone.

Figure 18:
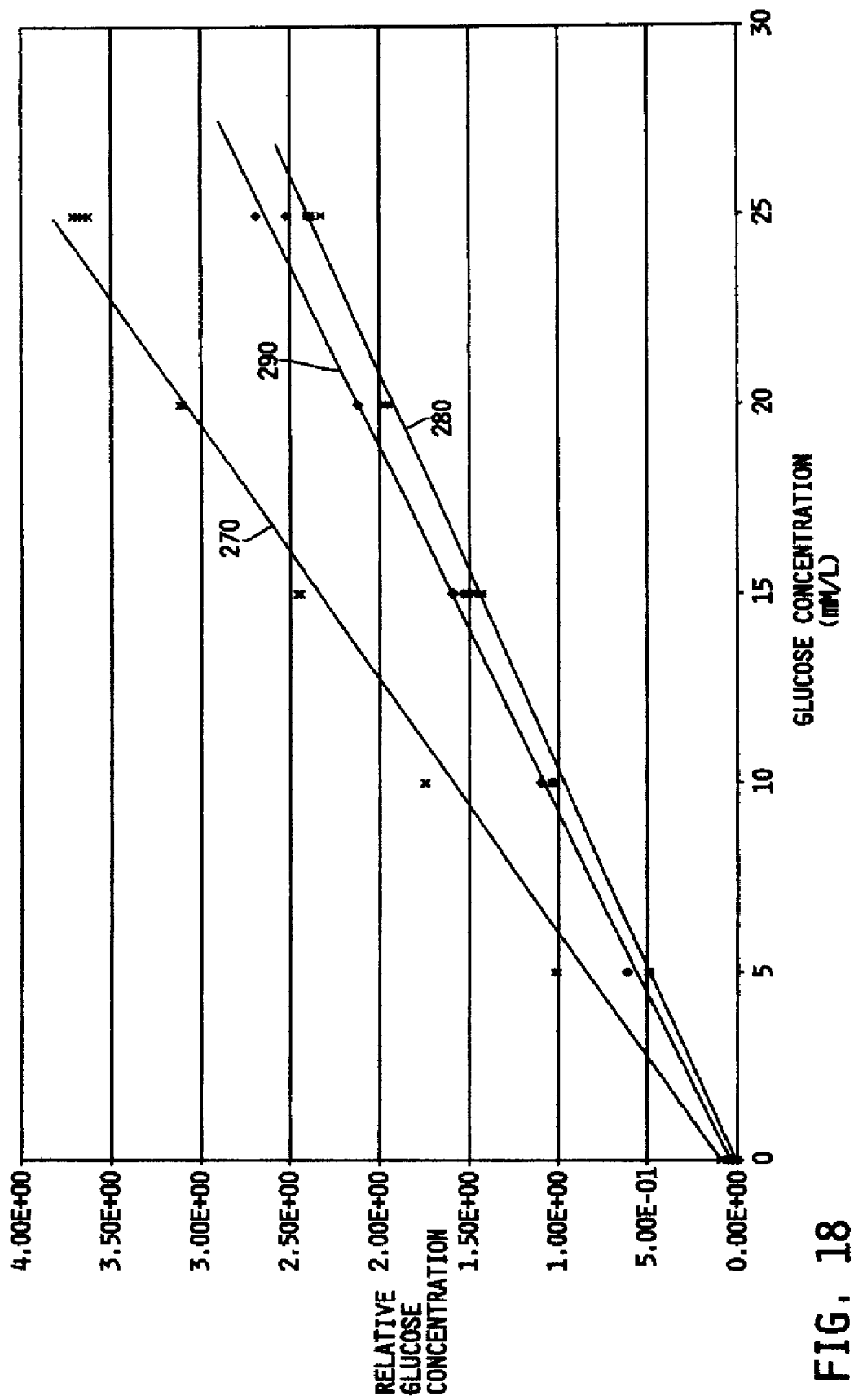
FIG. 18 is a plot of relative glucose concentration vs. actual glucose concentration resulting from the normalized DC sensor response, the admittance value of the resistor $R_2$ and the ratio of the DC senor response and the admittance value of the resistor $R_1$.

FIG. 18 is a plot of relative glucose concentration vs. actual glucose concentration resulting from processing by the processor 70 of the various DC, AC and AC-corrected sensor responses illustrated in FIG. 17. The relative glucose concentration 270 corresponds to the measured glucose concentration as determined by the processor 70 from the DC sensor response alone, the relative glucose concentration 280 corresponds to the measured glucose concentration as determined by the processor 70 from the admittance value, $Y_2$, alone, and the relative glucose concentration 290 corresponds to the measured glucose concentration as determined by the processor 70 from the ratio, $DC/Y_1$. It can be seen from FIG. 18 that the normalized admittance value, $Y_2$, alone tracks actual glucose more accurately than the DC response alone, and that the normalized ratio, $DC/Y_1$, tracks actual glucose more accurately than either the DC response alone or the admittance value, $Y_2$, alone.

Example 2

Figure 19:
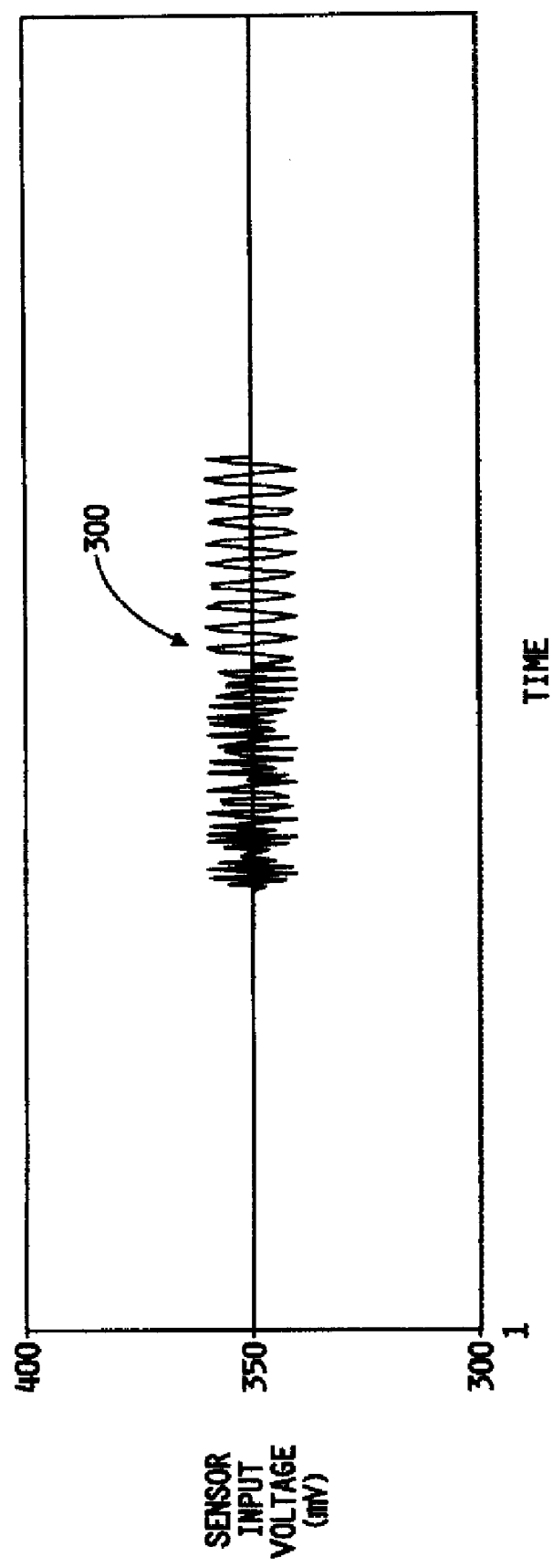
FIG. 19 is a plot of a portion of an interleaved sensor input signal vs. time comprising a DC component and a multiple-frequency AC component in a second experimental set up.

In this example, the sensor was the sensor 10' described in Example 1, but with a slightly thicker membrane disposed over the working electrode 24. The sensor 10' was placed in a conventional flow cell that was fluidly coupled to a conventional 2-channel high performance liquid chromatography pump (HPLC). The pump was again controlled to produce the glucose concentration (mM/L) vs. time profile 200 illustrated in FIG. 10 (over approximately a two and one-half day period). The potentiostat 70 was configured to apply an interleaved DC and AC potential signal with varying frequency content. The interleaved signal included a time-varying (AC) voltage of approximately 25 mV rms that was superimposed on a constant (DC) voltage of approximately 350 mV at intervals of approximately every 16-17 minutes. The interleaved input voltage was applied to the sensor 10' as described in Example 1 above, and the frequency of the time-varying signal content was swept from 100,000 Hz to 0.01 Hz with a step size of 5 frequency equally-spaced divisions per decade on a log scale to produce 36 different frequency values. An example of a portion of the interleaved input voltage 300 is illustrated in FIG. 19. The current through the working electrode 24 was monitored as the output of the sensor 10'. DC current measurements were taken between applications of the AC voltage, and AC current measurements were taken at each of the 36 different frequencies. The complex frequency values were computed as described in Example 1.

Figure 20:
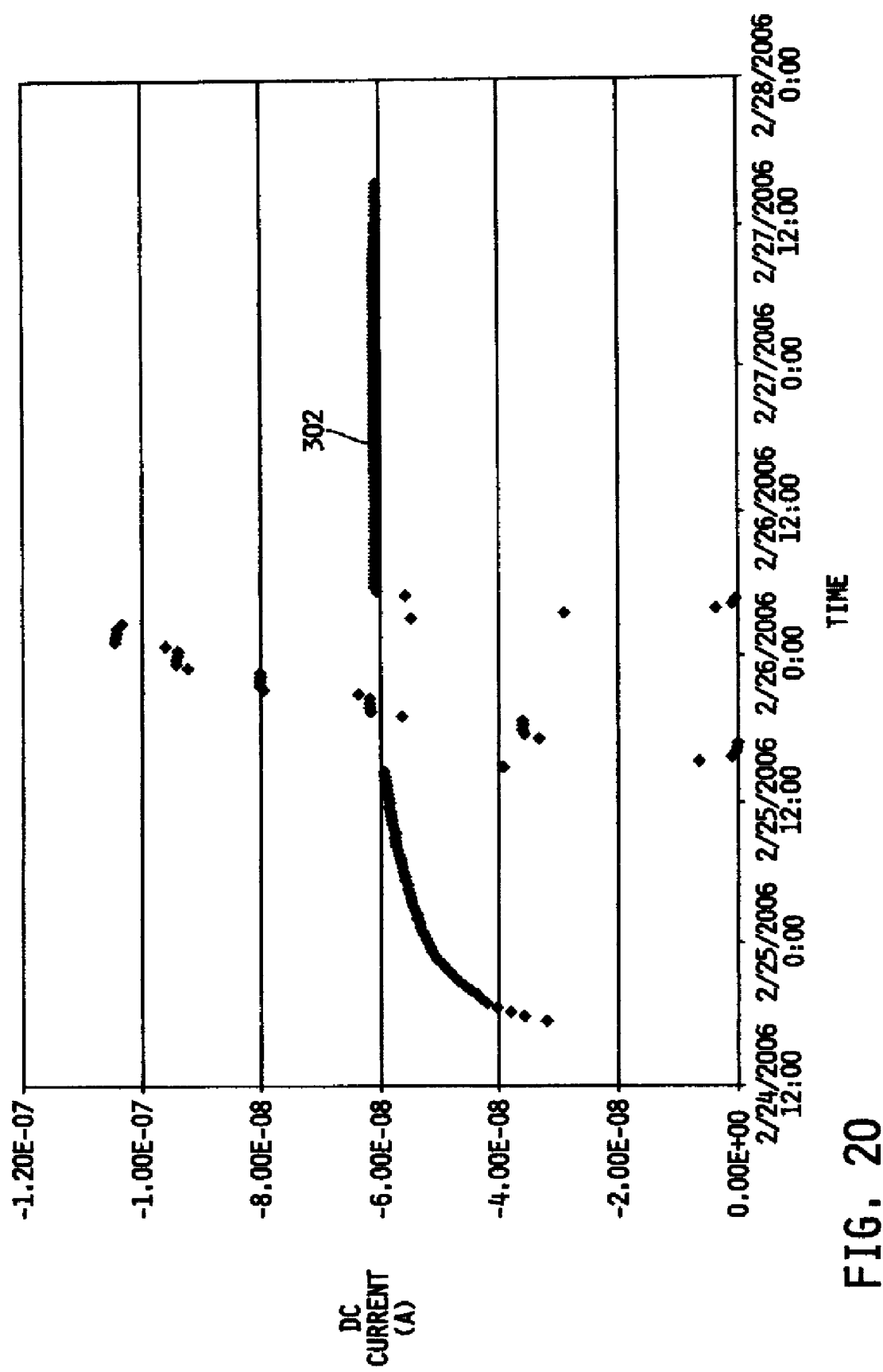
FIG. 20 is a plot of the DC current response vs. time of the continuous analyte sensor in the second experimental set up.

FIG. 20 is a plot of the DC current 302 produced by the sensor 10' vs. time using the same time scale used in Example 1 above. The DC current values were measured between application and measurement of the AC voltages. The DC current 302 produced by the continuous analyte sensor 10 is illustrative of the drift typically observed in the DC response during the break-in period, e.g., the first 24 hours or so, of a conventional continuous analyte sensor.

Figure 21:
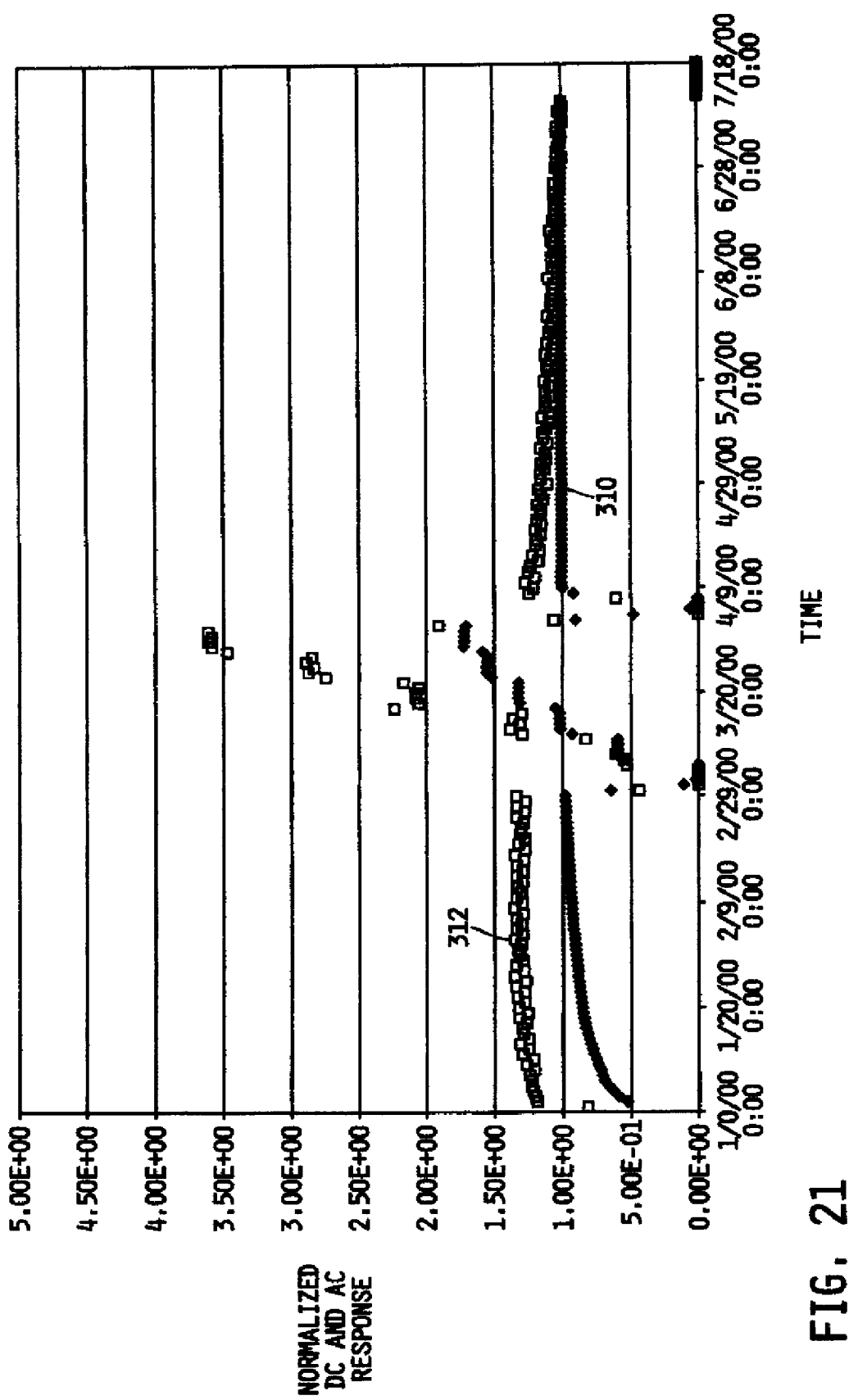
FIG. 21 is a plot of normalized DC and AC responses vs. time of the continuous analyte sensor according to an equivalent circuit model in the second experimental setup.
Figure 22:
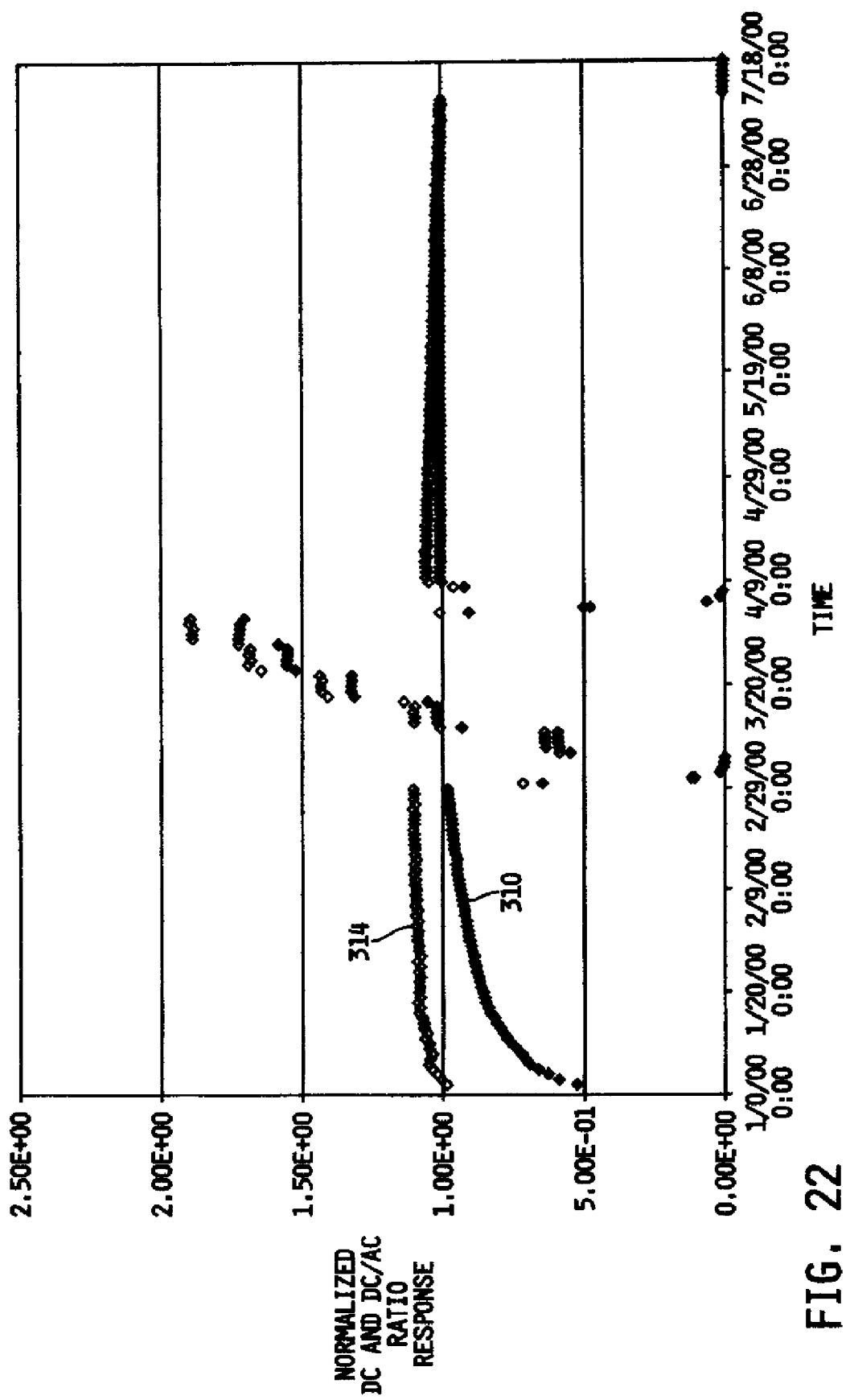
FIG. 22 is a plot of normalized DC and DC/AC ratio responses vs. time of the continuous analyte sensor according to the equivalent circuit model in the second experimental setup.

The complex impedance values were processed in this example according to three different complex impedance model processing techniques. The first technique involved processing the complex impedance values in accordance with the equivalent circuit model of the sensor as described in detail hereinabove in Example 1. In particular, the complex impedance values (magnitude and phase) for each AC voltage application that was applied over 31 frequencies ranging from 10,000 Hz to 0.01 Hz were fit to equations (1)-(4) above to using conventional non-linear regression techniques to produce a single set of equivalent circuit component values for each AC voltage application. FIG. 21 is a plot of the normalized DC response 310 of the sensor 10' and the admittance value, $Y_2$, 312 vs. time, and FIG. 22, is a plot of the normalized DC response 310 of the sensor 10' and a ratio 314 of the DC sensor response and the capacitance value, CPE1, e.g., DC/CPE1, vs. time, wherein $Y_2$ 312 and DC/CPE1 314 have each been normalized to have a final or last value of 1. As compared with the normalized DC response 310 of the sensor 10', the normalized admittance value, $Y_2$, 312 exhibits less drift over time, and with the continuous analyte sensor 10' of this example, the AC response of at least one of the components of the equivalent circuit model of the sensor 10, e.g., $Y_2$, 312, may thus be used alone to provide more accurate sensor data over time than the DC response alone. The ratio DC/CPE1 314 exhibits even less drift over time than the DC response 310 and the AC response, $Y_2$ 312. Thus, by correcting the conventional DC response of the continuous analyte sensor 10 of this example with a time-varying (AC) impedance component of at least one of the components of the equivalent circuit model of the sensor 10, e.g., CPE1, the resulting analyte measurements will be more constant over time than analyte measurements based solely on the AC response of the at least one of the components of the equivalent circuit model of the sensor 10 of this example, and will be substantially more constant over time than analyte measurements based solely on the DC response of the sensor 10.

The complex impedance values in this example were also processed by the processor 70 according to a conventional principle component analysis. In this analysis, the equivalent circuit component values for each of the seven decades of frequencies between 100,000 Hz and 001 Hz were processed to statistically determine seven corresponding principle components, and the four principle components having the highest principle component score were chosen to fit to the following principle component model equations:

$$\text{Predicted Glucose} = I_O + S0*(DC + aDC^2) + S1*PC1 + S2*PC2 + S3*PC3 + S4*PC4 \quad (5),$$

$$PC_n = \Sigma(a_i)_n * C_i \quad (6),$$

where $I_O$ is an intercept value, "i" ranges from 1-7, "n" ranges from 1-4 and the summation is conducted over the range of "i". It will be understood that more or fewer principle components may be determined and used to predict or estimate analyte measurement values.

Figure 23:
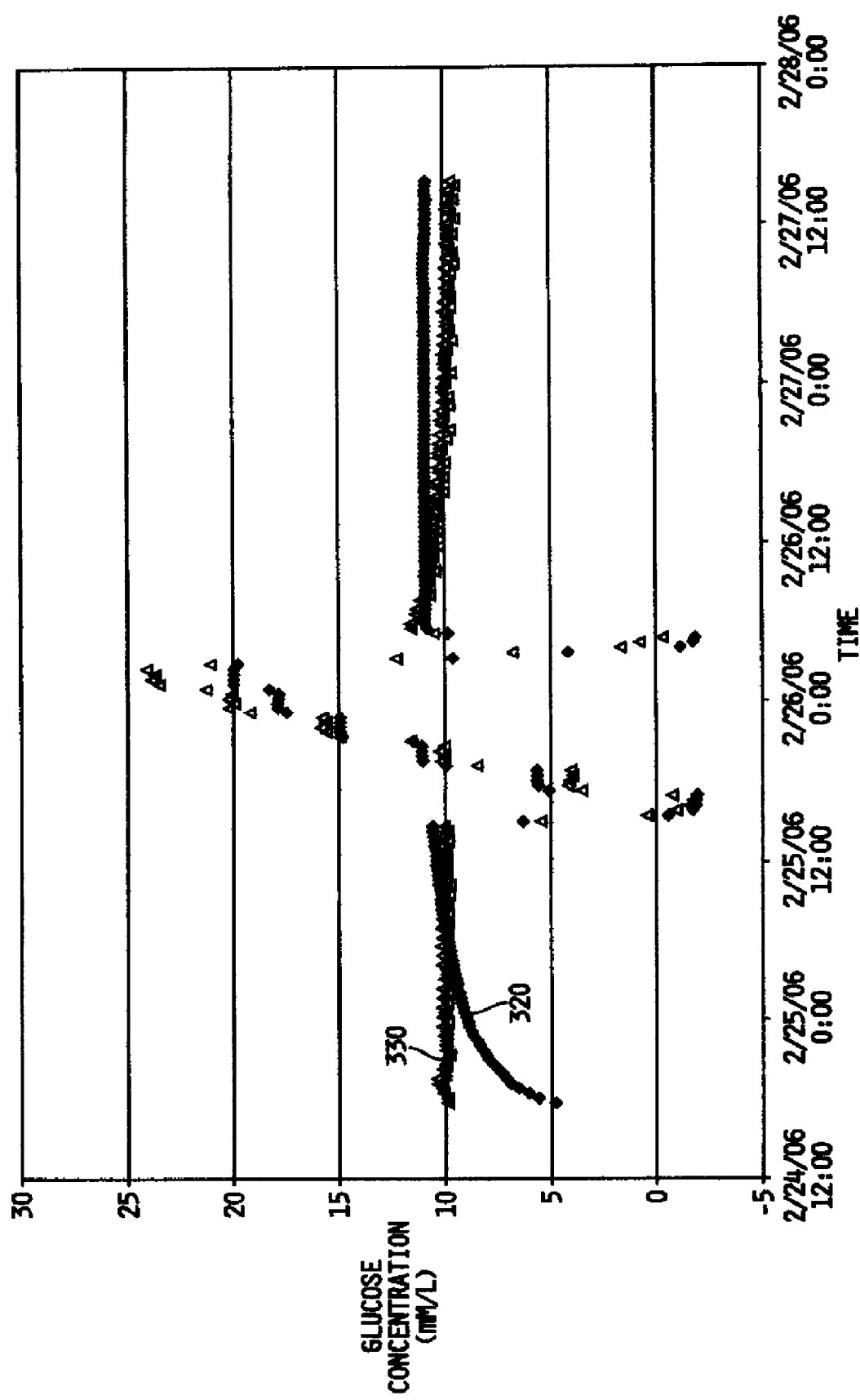
FIG. 23 is a plot of predicted glucose concentration vs. impedance scan of the continuous analyte sensor according to a principal component model in the second experimental setup.

Thus, each of the 200 applications of the AC input voltage yielded 200 sets of equations (5) and (6). FIG. 23 is a plot of the predicted glucose concentration 320 using the conventional DC response of the sensor 10, along with the predicted glucose concentration 330 using the equivalent circuit component values processed according to equations (5) and (6). FIG. 23 thus reveals that principle component analysis may alternatively or additionally be used to process the complex impedance information produced by the sensor 10 of this example in response to time-varying input signals to produce resulting analyte measurements that are substantially more constant over time than analyte measurements based solely on the DC response of the sensor 10. This is particularly true for the initial break-in period, e.g., first 24 hours or so, of operation of the continuous analyte sensor 10, as illustrated in FIG. 23.

The complex impedance values in this example were additionally processed by the processor 70 according to a conventional second order empirical model. In this analysis, the equivalent circuit component values at four frequencies between 100,000 Hz and 001 Hz were processed to fit to the following empirical model equations:

$$\text{Predicted Glucose} = \text{Slope}*(DC + a*DC^2) \quad (7),$$

$$\text{Slope} = \text{Exp}(A + Yr\_eff + Yi\_eff) \quad (8),$$

$$Yr\_eff = (d1*Yr1 + d2*Yr2 + d3*Yr3 + d4*Yr4) \quad (9),$$

$$Yi\_eff = (e1*Yi1 + e2*Yi2 + e3*Yi3 + e4*Yi4) \quad (10).$$

In this particular experiment, conventional model optimization techniques were used to determine values of the four frequencies of 63 kHz, 0.1 Hz, 0.063 Hz, 0.01 Hz. It will be understood, however, that more, fewer and/or different frequencies may alternatively be used.

Figure 24:
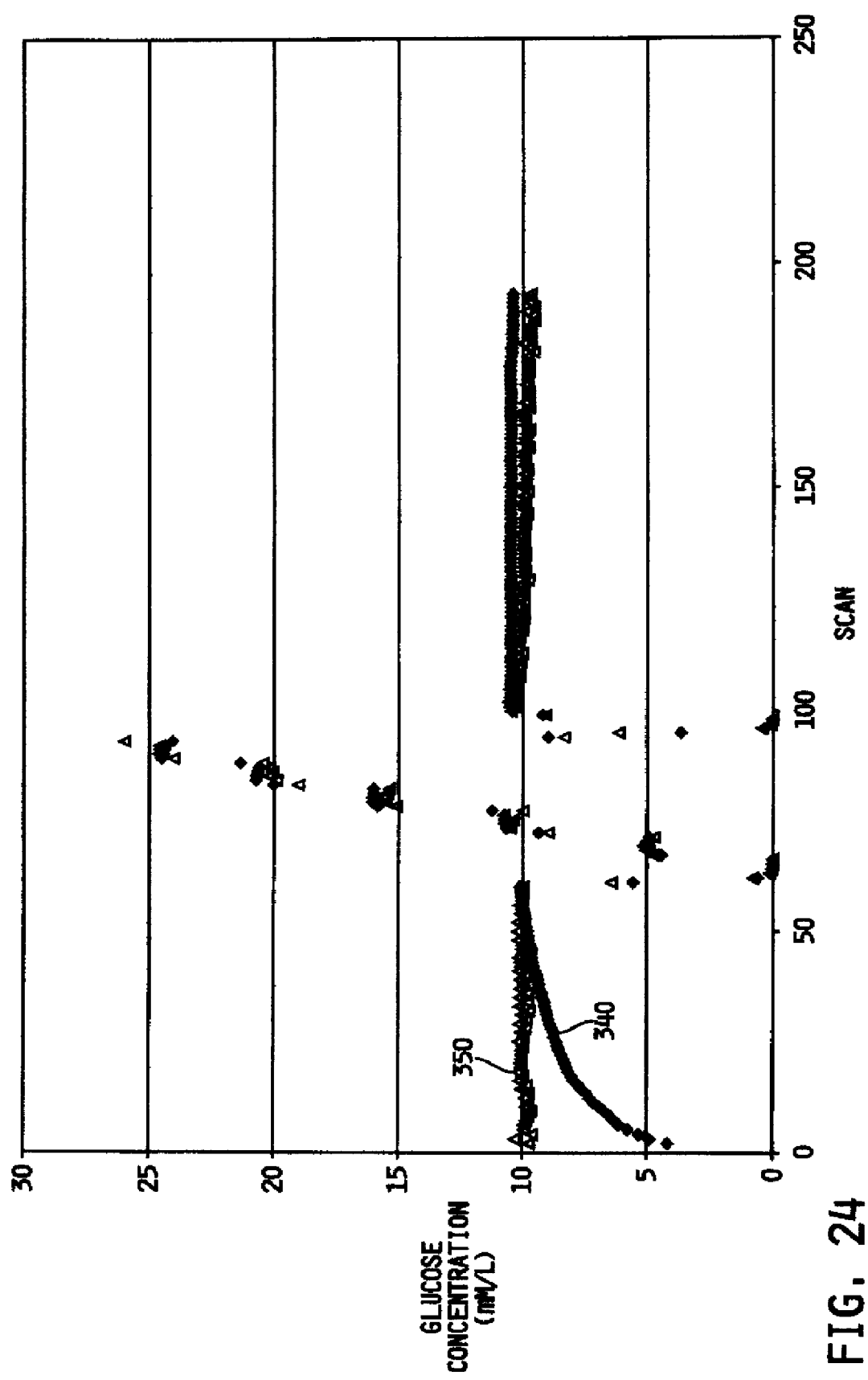
FIG. 24 is a plot of predicted glucose concentration vs. impedance scan of the continuous analyte sensor according to an empirical model in the second experimental setup.

Each of the 200 applications of the AC input voltage yielded 200 sets of equations (7)-(10). FIG. 24 is a plot of the predicted glucose concentration 340 using the conventional DC response of the sensor 10, along with the predicted glucose concentration 350 using the equivalent circuit component values processed according to equations (7)-(10). FIG. 24 reveals that the empirical model defined by equations (7)-(10) may alternatively or additionally be used to process the complex impedance information produced by the sensor 10' of this example in response to time-varying input signals to produce resulting analyte measurements that are substantially more constant over time than analyte measurements based solely on the DC response of the sensor 10'. Again, this is particularly true for the initial break-in period, e.g., first 24 hours or so, of operation of the continuous analyte sensor 10' of this example.

Example 3

In this example, the sensor 10' was prepared identically to the sensor used in Example 1. The sensor 10' was placed in a conventional flow cell that was fluidly coupled to a conventional 2-channel high performance liquid chromatography pump (HPLC). The pump was controlled to produce a glucose concentration (mM/L) vs. time profile similar to that illustrated in FIG. 10, but in this example the glucose concentration was set at a constant 10 mM/L for a break-in period of approximately 1 day, after which a profile of glucose concentrations was applied to the sensor 10 for approximately 12 hours. Following the glucose profile, the glucose concentration was again set at a constant 10 mM/L for approximately 18 hours before applying another glucose profile. The potentiostat 70 was configured in a conventional manner to apply a constant (DC) voltage of approximately 350 mV between the working electrode 24 and the reference electrode 28. The DC voltage was then used in an internal feedback path to modulate a time-varying (AC) current applied to the counter electrode 32 at intervals of approximately every 16-17 minutes, which resulted in a time-varying (AC) voltage of approximately 5 mV rms between the working electrode 24 and the reference electrode 28 at intervals of approximately every 16-17 minutes. The frequency of the time-varying voltage was swept from 100,000 Hz to 0.01 Hz with a step size of 2 equally-spaced frequency divisions per decade on a log scale to produce 15 different frequency values per frequency sweep. The current through the working electrode 24 was monitored as the output of the sensor 10'. DC output current measurements were taken by passing the output current values through a low-pass filter algorithm stored in the memory 74 and executed by the processor 72, and AC output current measurements were taken by passing the output current values through a high-pass filter algorithm stored in the memory 74 and executed by the processor 72. A complex impedance vector, Z, was determined at each frequency sweep as a function of a vector, I, of the AC output current measurements and a vector, E, of corresponding AC input voltage values, e.g., $Z=E/I$, wherein each of the vectors Z, I and E contain 15 different impedance, current and voltage values respectively.

Figure 25:
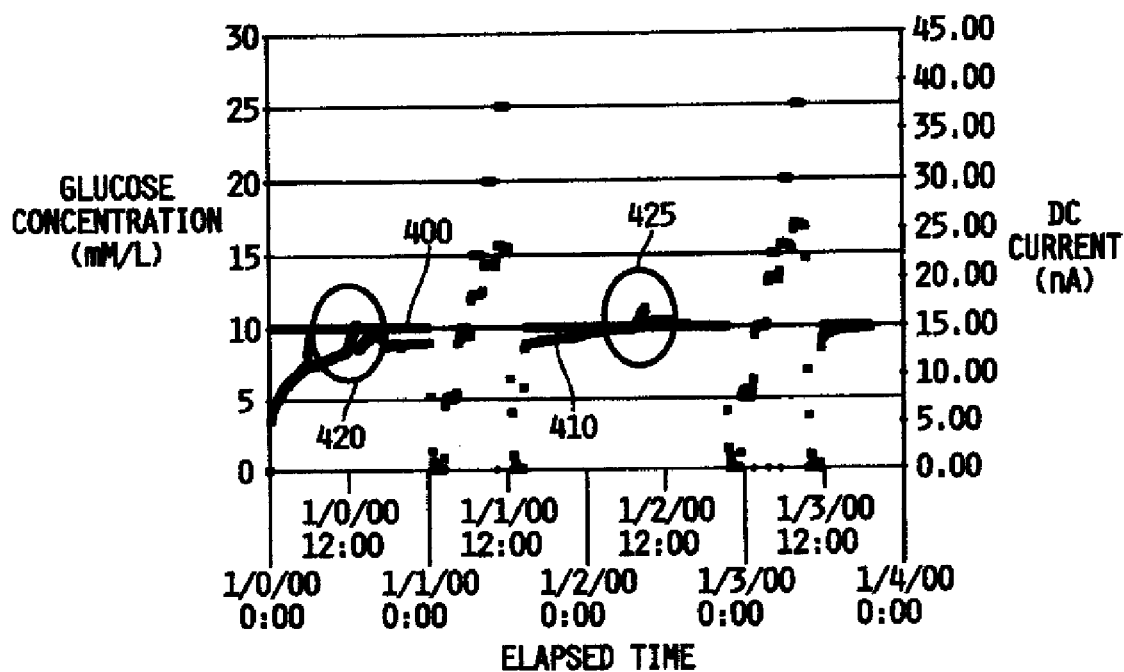
FIG. 25 is a plot of a glucose concentration profile, along with the DC current produced by the sensor, vs. time in a third experimental setup.

FIG. 25 is a plot of the glucose concentration profile 400, along with the DC current 410 produced by the sensor 10', vs. time. The DC current 410 illustrates the change in sensitivity of the continuous analyte sensor 10' that is typically observed during the break-in period of the sensor 10'. The DC current 410 additionally includes a number of anomalies 420 and 425 that are remote from the glucose profiles and that are not related to the glucose concentration of the sample. Anomalies 420, 425 of the type shown in FIG. 25 are sometimes observed in continuous analyte sensor data, and such anomalies further limit the usefulness of the sensor data, such as when such data is used to control insulin infusion.

Figure 26:
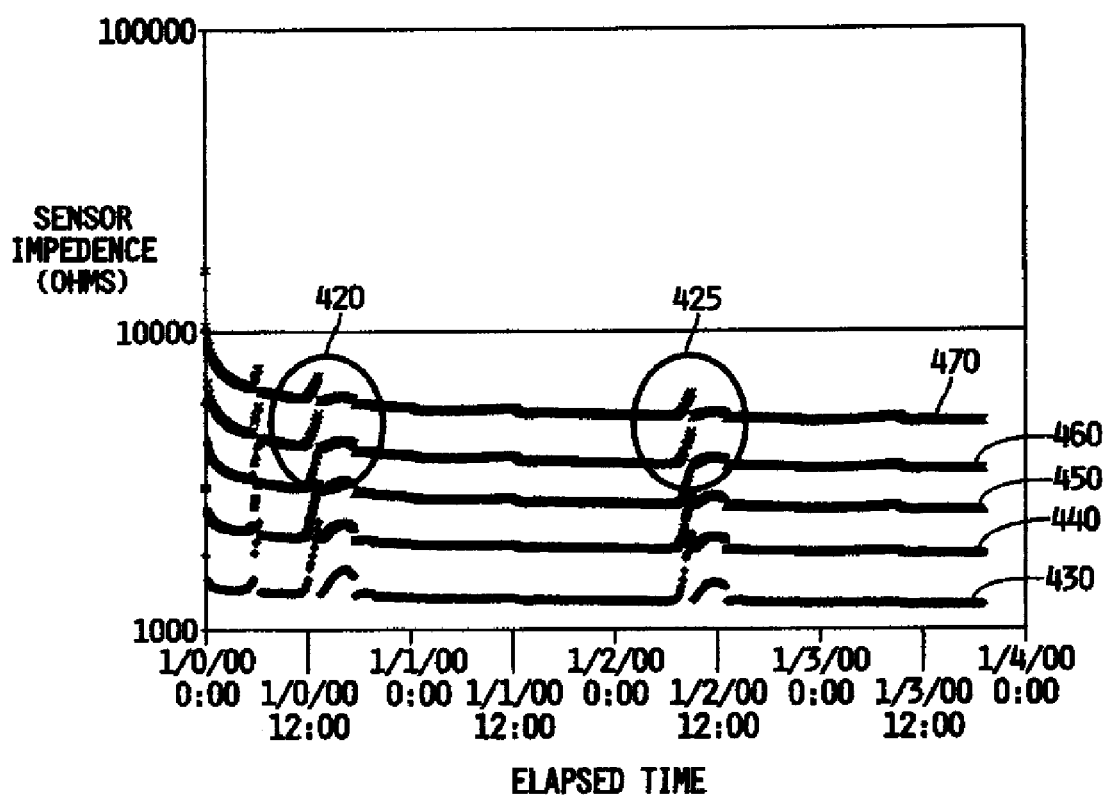
FIG. 26 is a plot of sensor impedance vs. time illustrating the AC response of the sensor in the third experimental setup.

FIG. 26 is a plot of the magnitude of the complex impedance, Z, (on a log scale) vs. time illustrating the AC response of the sensor 10 at various frequencies. The plot of FIG. 26 shows the computed impedance values of the sensor 10' over time at five different frequencies. The impedance 430 represents the sensor impedance at 100 kHz, and the impedances 440, 450, 460 and 470 represent sensor impedances at successively lower frequencies of 31 kHz, 10 kHz, 3.1 kHz and 1 kHz respectively. It can be observed from FIG. 26 that the magnitudes of the anomalies 420 and 425 decrease with decreasing frequencies as the frequency is reduced toward DC, although the anomalies clearly return at DC levels as shown in FIG. 25. The complex impedance, Z, of the sensor 10' at appropriately low frequencies can thus be used to compute analyte concentration values with a reduced impact of the anomalies 420, 425 than are present in analyte concentration values based solely on the DC response 410 of the sensor 10'. Alternatively, the complex impedance, Z, of the sensor at appropriately high frequencies can be used to compensate the DC response 410 for the purpose of not only reducing the drift of the sensor 10 over time but to also reduce the impact of the anomalies 420, 425 on the computed analyte concentration values. Alternatively still, the complex impedance, Z, of the sensor at one or more appropriate frequencies can be used to detect anomalies in the sensor data, such as the anomalies 420, 425, and to notify the system of potential sensor data quality issues when such anomalies are detected.

Figure 27:
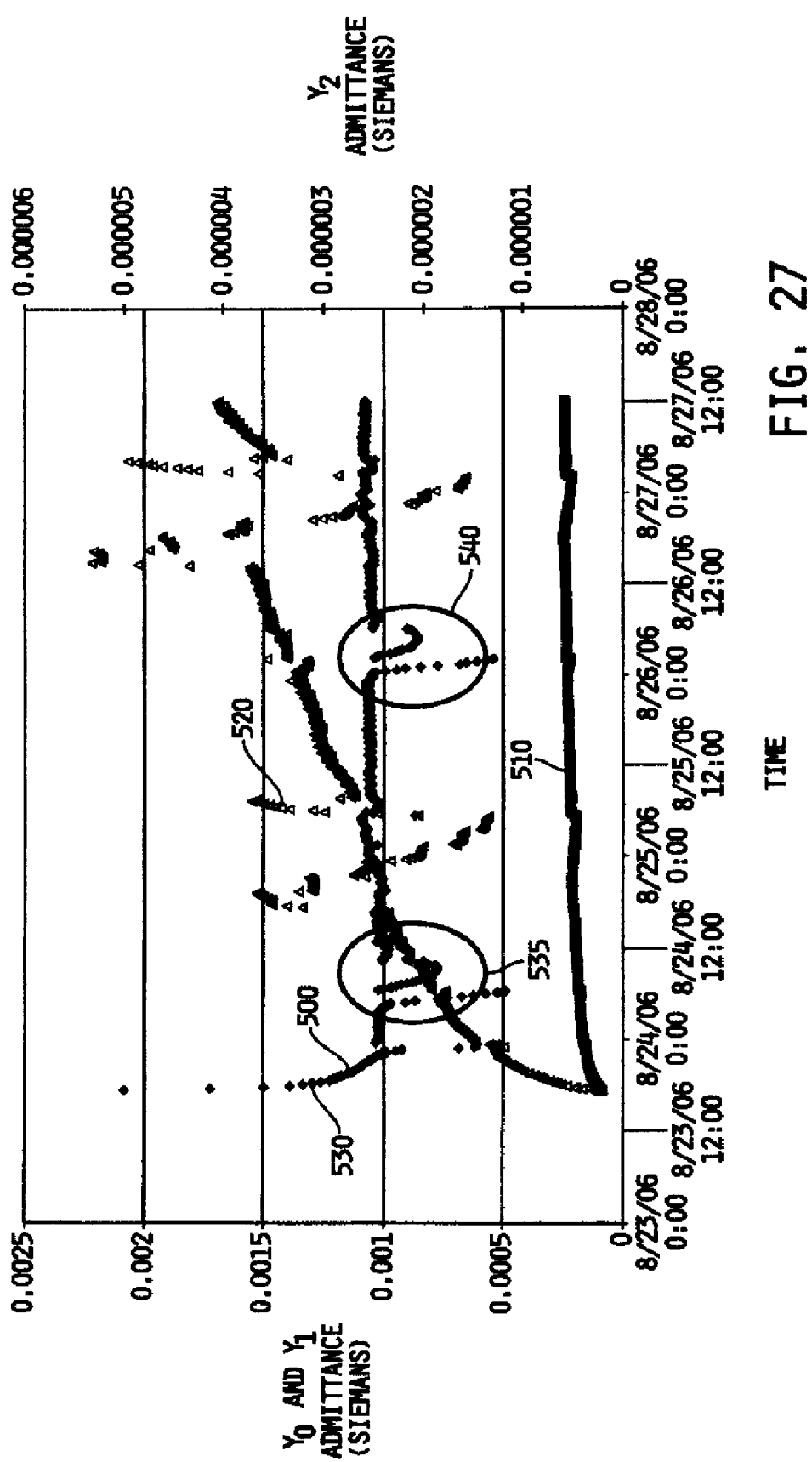
FIG. 27 is a plot of the $Y_0$, $Y_1$ and $Y_2$ admittance component values of the equivalent circuit model of the sensor vs. time in the third experimental setup.

The complex impedance data in this example was further processed according to equations (1)-(4) above to determine an equivalent circuit model of the sensor 10 as described hereinabove with respect to Example 1. FIG. 27 is a plot of the $Y_0$, $Y_1$ and $Y_2$ admittance components 500, 510 and 520 respectively, of the equivalent circuit model of the sensor 10 vs. time. Like the DC current 410, the $Y_2$ component 520 illustrates the change in sensitivity of the continuous analyte sensor 10 that is typically observed during the break-in period of the sensor 10', and is also sensitive to changes in the analyte concentration profile. The $Y_0$ component 500 is not sensitive to changes in the analyte concentration profile, although the initial portion 530 $Y_0$ component 500 appears to be more sensitive to the initial sensor break-in period than the $Y_2$ component. Furthermore, the $Y_0$ component 500 is the only one of the admittance components that is sensitive to the signal anomalies 535 and 540. Otherwise, the $Y_0$ component 500 remains relatively constant. The $Y_0$ component may thus be monitored, in this example, to provide an indication of when the sensor 10 is stable and is producing useful and reliable data. For example, the electronic circuitry 64 may, in this example, be configured to monitor $Y_0$ 500, such as by monitoring its rate of change or magnitude, and to determine that the sensor data is stable and reliable only when the rate of change of $Y_0$ is within one or more predetermined rate of change or magnitude boundaries. When the sensor data is outside of the one or more predetermined boundaries, the electronic circuitry 64 may consider the sensor data unreliable and/or unstable, and disregard such sensor data and/or request or otherwise undertake a sensor calibration or recalibration procedure. It should be noted that in other implementations of a continuous analyte sensor, one or more additional or other equivalent circuit model components may be sensitive to sensor stability, and may therefore be used either alone or in combination, or a function of such one or more equivalent circuit model components, as a monitor of sensor stability.

Example 4

The concepts of this disclosure are applicable to sensors that operate according to the principle of Microdialysis. One example of such a system is described in the publication Michael Schoemaker, et al., *The SCGM1 System: Subcutaneous Continuous Glucose Monitoring Based on Microdialysis Technique*, Diabetes Technology & Therapeutics, Vol. 5, Number 4 (2003), the disclosure of which is incorporated herein by reference. The system described in the Shoemaker et al. publication utilizes a subcutaneous catheter to provide a bodily fluid sample to an electrochemical sensor that resides external to the body of the subject, and the sensor is used to measure the subject's glucose concentration. Other microdialysis systems are described in U.S. Pat. Nos. 6,091,976, 6,434,409 and 6,591,126, the disclosures of which are each incorporated herein by reference.

One common drawback associated with such microdialysis or microperfusion sensor systems is a variable and unknown recovery of the analyte from the subject's tissue to the dialysis solution. One proposed technique for improving the accuracy of the analyte measurements is to use a so-called ionic reference. This involves measuring the concentration of another species in the dialysis solution which is known to be more constant in the body tissue having the analyte of interest, and using this measurement to compensate or correct analyte measurements. In the case where the analyte is glucose concentration, the other species that may be, for example, sodium (Na) or potassium (K). Examples of systems and techniques for measuring and/or using such an ionic reference are disclosed in U.S. Pat. Nos. 5,097,834, and 5,193,545, 7,022,071, the disclosures of which are each incorporated herein by reference.

Figure 28:
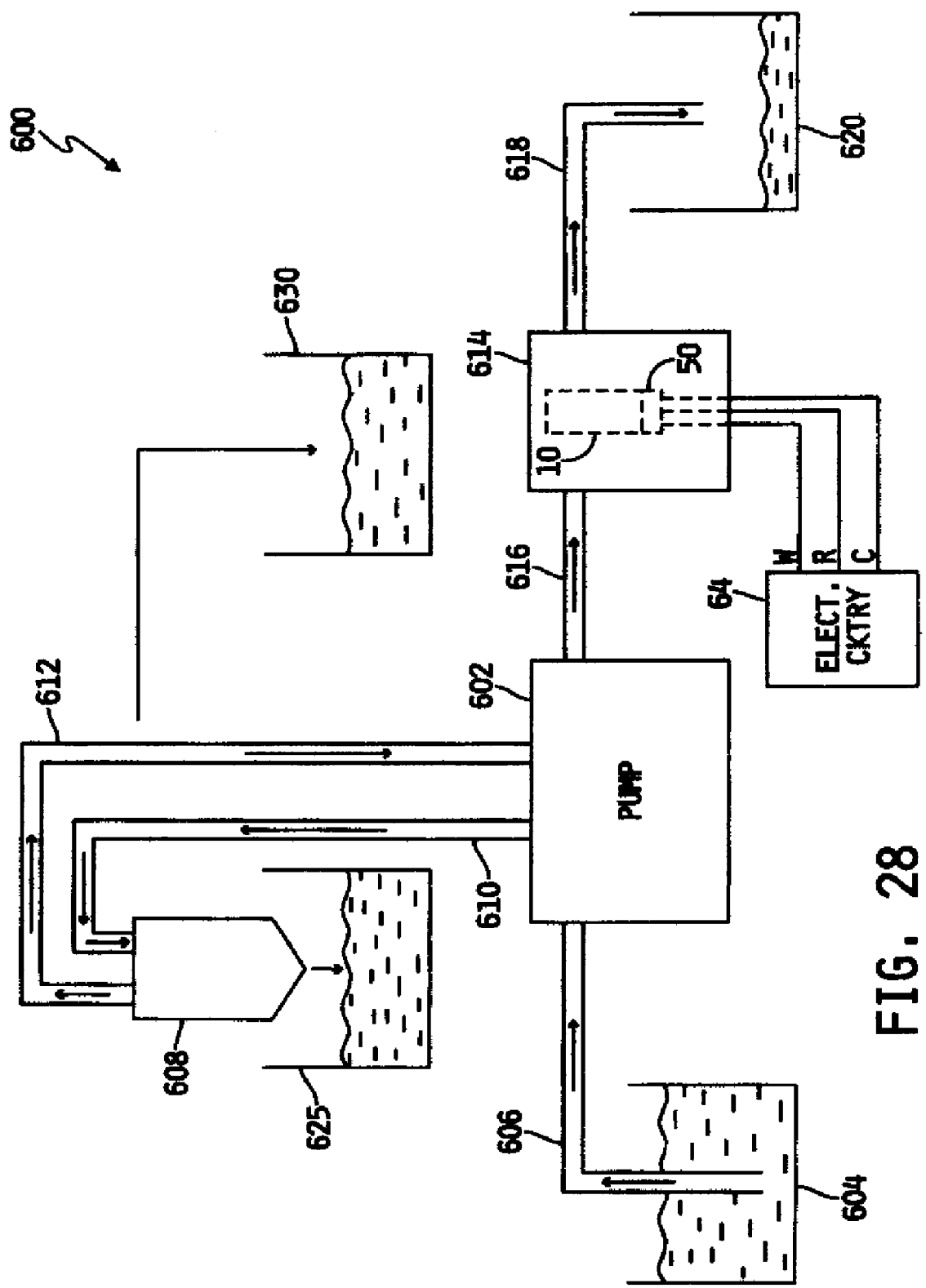
FIG. 28 is a diagram of a fourth experimental setup using a conventional flow cell was used to investigate and demonstrate the applicability of some of the concepts of this disclosure to the recognition and quantification of differences in analyte recovery in a system operating in accordance with the principle of microdialysis.

In this example, as shown in FIG. 28, an experimental system using a conventional flow cell was used to investigate and demonstrate the applicability of some of the concepts of this disclosure to the recognition and quantification of differences in analyte recovery in a system operating in accordance with the principle of microdialysis. Referring to FIG. 28, the experimental system 600 includes a pump 602 having a first pump inlet fluidly coupled to a source of a perfusate 604 via a fluid passageway 606. In the illustrated embodiment, the pump 602 is a conventional peristaltic pump, and the perfusate is 5% Mannitol in water. A first outlet of the pump 602 is fluidly coupled to a catheter 608 via a fluid passageway 610, and a second inlet of the pump 602 is also fluidly coupled to the catheter 608 via a fluid passageway 612. A second outlet of the pump 602 is fluidly coupled to an inlet of a flow cell 614 via a fluid passageway 616, and an outlet of the flow cell 614 is fluidly coupled to a waste reservoir 620 via a fluid passageway 618. The pump 602 is operable to pump the perfusate 604 through the fluid passageways 606 and 610 and into the catheter 608, and to also pump fluid from the catheter 608 through the fluid passageways 612 and 616 and into the flow cell 614. Fluid exits the flow cell 614 via the fluid passageway 618.

The continuous analyte sensor 10 is positioned within the flow cell 614 so that fluid pumped through the flow cell 614 by the pump 602 flows over the sensor 10. The sensor 10 is electrically connected via the connector 50 to the electronic circuitry 64. In the experimental system 600 illustrated in FIG. 28, the reagent layer 36 disposed over the working electrode 24 of the sensor 10 is Glucose Oxidase. In the illustrated example, the catheter 608 was alternately placed in contact with two different sample solutions 625 and 630. The sample solution 625 comprised glucose in 100% 10 mM NaPO4/150 mM NaCl, and the sample solution 630 comprised glucose in 80% mM NaPO4/150 mM NaCl to 20% water. Assuming 100% recovery in the catheter 608, the two different solutions 625 and 630 thus represent and model the effects of a change in recovery of glucose in a human subject.

In the experiment, the pump 602 drove the perfusate 604 through the fluid passageways 606, 610 and through the catheter 608 into the sample solution 625, 630, and from the sample solution 625, 630 through the catheter 608, the fluid passageways 612, 616, and through the flow cell 614 into the waste reservoir 620. The catheter 608 was placed in one of the sample solutions 625, 630, and at intervals, moved to the other sample solution 625, 630. The sensor 10 was electrically exercised as described above in example 2, except that the frequency of the time-varying voltage was swept from 100,000 Hz to 0.01 Hz with a step size of 2 equally-spaced frequency divisions per decade on a log scale to produce 15 different frequency values per frequency sweep. The current through the working electrode 24 was monitored as the output of the sensor 10, and DC output current measurements were taken by passing the output current values through a low-pass filter algorithm stored in the memory 74 and executed by the processor 72. AC output current measurements were taken by passing the output current values through a high-pass filter algorithm stored in the memory 74 and executed by the processor 72. A complex frequency vector, Z, was determined at each frequency sweep as a function of a vector, I, of the AC output current measurements and a vector, E, of corresponding AC input voltage values, e.g., Z=E/I, wherein each of the vectors Z, I and E contain 36 different impedance, current and voltage values respectively.

The following Table illustrates the results of the above measurements in an experiment including four separate flow cells 614 arranged in parallel and simultaneously receiving the same fluid from the pump 602. The average values in the Table represent the algebraic averages of values produced by identically configured sensors 10 in each of the four separate flow cells 614, and the delta values represent measurements with the catheter 608 in the solution 630 subtracted from measurements with the catheter 608 in the solution 625.

TABLE

|  | ΔDC | % ΔDC | ΔZ | % ΔZ |
|---|---|---|---|---|
| Average | −0.05379 | −1.8 | −780.443 | −10.5 |
| Std. Dev. |  | 5.2 |  | 1.6 |

The DC values in the above Table, which are indicative of glucose concentration, are on average not substantially different between the solutions 625 and 630. However, the complex impedance, Z, at 1000 Hz is significantly higher in the solution 630 (80% mM NaPO4/150 mM NaCl to 20% water) than in the solution 625 (100% 10 mM NaPO4/150 mM NaCl). The complex impedance measurements are thus capable of recognizing a reduced recovery of the catheter 608 independently of the DC values. With this quantitative measurement, a compensated (corrected) and more accurate analyte value than is available from the DC measurements alone may be determined based on the DC and complex impedance values. Alternatively or additionally, an error condition may be detected based on the complex impedance value. This information may be used, for example, to limit the analyte information by disregarding analyte information obtained during the error condition.

Example 5

In this example, the experimental system 600 of Example 4 was modified such that only a single sample solution of constant glucose concentration was used, and the catheter 608 was immersed in this sample solution for an extended time period. In this example, the single sample solution had a glucose concentration of 8.0 mM/L.

Figure 29:
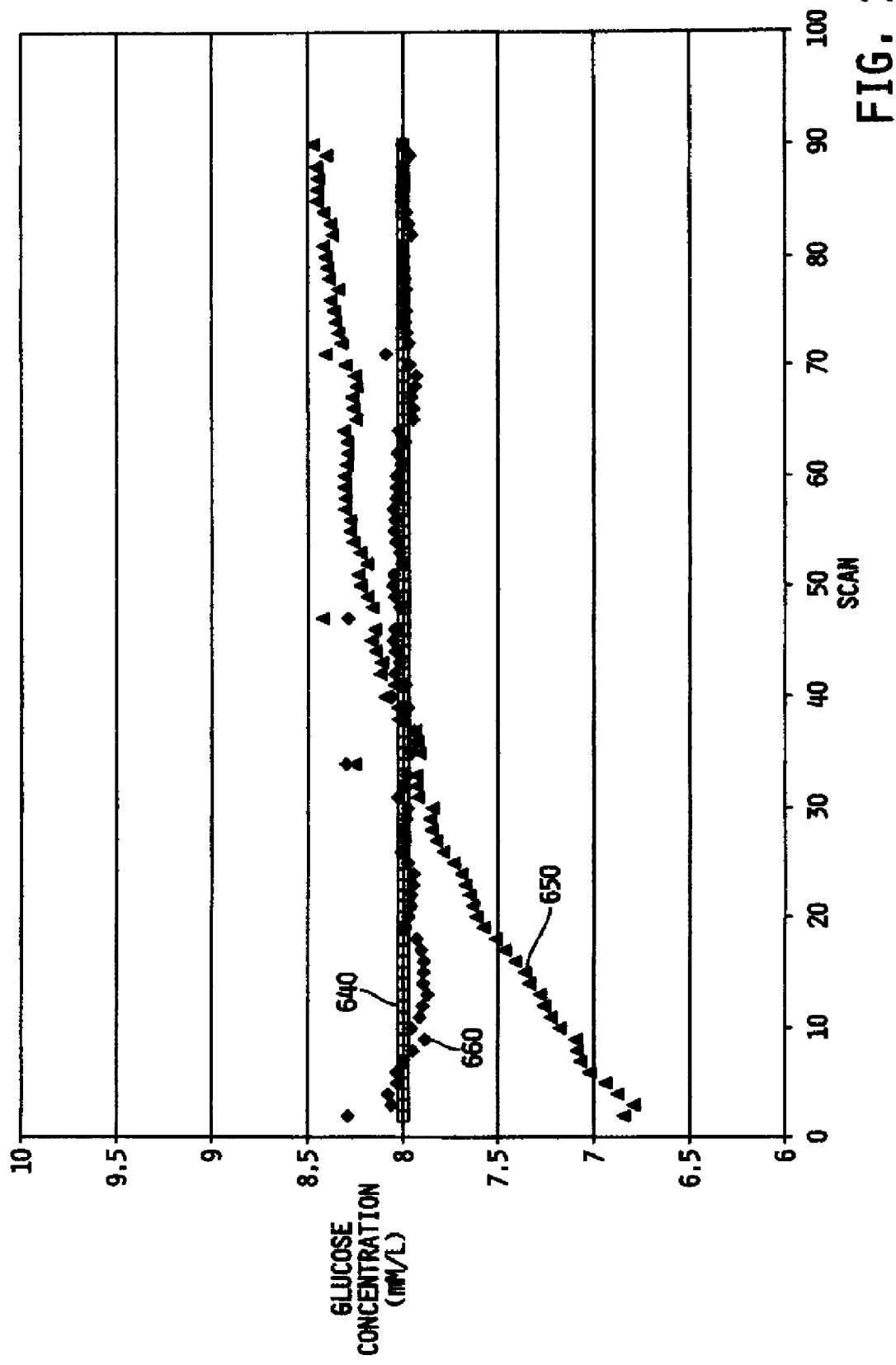
FIG. 29 is a plot of the predicted glucose concentration vs. impedance scan of the conventional DC response of the sensor, a predicted glucose concentration calculated using the DC current response compensated by the equivalent circuit model component(s) and the known glucose concentration, according to the fourth experimental setup.

The sensor 10 in this example was electrically exercised, while being exposed to the combination of the sample solution and the perfusate, as described above in Example 2, and component values of an equivalent circuit of the type illustrated in FIG. 12 were determined using equations (1)-(4) above. One or more of the component values was/were then used as described hereinabove with respect to Examples 1 and 2 to compensate for the changing sensitivity of the sensor 10 over time. FIG. 29 is a plot of glucose concentration 650 computed using the conventional DC response of the sensor 10, along with glucose concentration 660 computed using the DC current response 650 compensated by the equivalent circuit model component(s), as compared with the known glucose concentration 640 of 8.0 mM/L. From FIG. 29, it can be seen that the complex impedance information can be used to compensate for the changing sensitivity during the initial sensor break in period, e.g., scans 1-40, as well as during operation of the sensor 10 after the initial break-in period, e.g., scans 41-90.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, those skilled in the art will recognize other technologies that may benefit from one or more of the concepts described herein, and the application of one or more of the concepts described herein to any such other technologies is contemplated by this disclosure.

What is claimed is:

1. A method of operating an electrochemical analyte sensor having one or more electrodes, comprising:
applying for a test period a time-varying input signal to at least one of the one or more electrodes,
monitoring a time-varying output signal produced by the sensor in response to application for the test period of the time-varying input signal,
determining a complex impedance of the sensor based on the time-varying input signal applied for the test period and on the time-varying output signal,
applying for an entirety of the test period a constant-valued DC input signal to the at least one of the one or more electrodes,
monitoring a DC output signal produced by the sensor in response to the application of the DC input signal, and
determining at least one measured value of the analyte based on the complex impedance of the sensor and on the DC output signal using a processor.

2. The method of claim 1 wherein determining at least one measured value of an analyte to which the sensor is exposed comprises:
selecting a mathematical model of the sensor having a number of model components,
fitting values of the complex impedance to the mathematical model of the sensor to determine values of the number of model components,
identifying one or a functional combination of the number of model components having a response over time that, when combined with the DC output signal, produces a sensor response that has minimal undesirable variations in magnitude over time, and
computing the at least one measured value of the analyte based on values of the identified one or functional combination of the number of model components and on the DC output signal.

3. The method of claim 2 wherein applying a time-varying input signal to at least one of the one or more electrodes comprises applying the time-varying input signal at a number of different frequencies.

4. The method of claim 2 further comprising:
identifying another one or a functional combination of the model components having a response over time that is substantially insensitive to variations in analyte concentration and sensor sensitivity,
identifying as stable only ones of the one or a functional combination of the number of model components for which the values of corresponding ones of the another one or a functional combination of the model components fall within a range of response values, and
using only the stable ones of the one or a functional combination of the number of model components to compute the at least one measured value of the analyte.

5. The method of claim 1 wherein applying for a test period a time-varying input signal to at least one of the one or more electrodes and applying for an entirety of the test period a constant-valued DC input signal to the at least one of the one or more electrodes together comprise applying a single input signal to the at least one of the one or more electrodes that has a time-varying component and a constant-valued DC component.

6. The method of claim 1 wherein the time-varying input signal and the constant-valued DC signal are separate signals each applied to the at least one of the one or more electrodes.

7. A method of operating an electrochemical analyte sensor having one or more electrodes, comprising:
applying a time-varying input signal to at least one of the one or more electrodes,
monitoring a time-varying output signal produced by the sensor in response to application of the time-varying input signal,
determining a complex impedance of the sensor based on the time-varying input and output signals, and
determining at least one measured value of an analyte to which the sensor is exposed based, at least in part, on the complex impedance,
wherein determining at least one measured value of an analyte to which the sensor is exposed comprises:
selecting a mathematical model of the sensor having a number of model components,
fitting values of the complex impedance to the mathematical model of the sensor to determine values of the number of model components,
identifying one or a functional combination of the number of model components having a response over time that produces a sensor response that has minimal undesirable variations in magnitude over time, and
computing the at least one measured value of the analyte based on values of the identified one or functional combination of the number of model components using a processor.

8. The method of claim 7 wherein applying a time-varying input signal to at least one of the one or more electrodes comprises applying the time-varying input signal at a number of different frequencies.

9. The method of claim 7 further comprising:
identifying another one or a functional combination of the model components having a response over time that is substantially insensitive to variations in analyte concentration and sensor sensitivity,
identifying as stable only ones of the one or a functional combination of the number of model components for which the values of corresponding ones of the another one or a functional combination of the model components fall within a range of response values, and
using only the stable ones of the one or a functional combination of the number of model components to compute the at least one measured value of the analyte.

10. A method of operating an electrochemical analyte sensor having one or more electrodes, comprising:
applying a time-varying input signal to at least one of the one or more electrodes,
monitoring a time-varying output signal produced by the sensor in response to application of the time-varying input signal,
determining a complex impedance of the sensor based on the time-varying input and output signals, and
determining from the complex impedance whether an output response of the sensor is stable by:
selecting a mathematical model of the sensor having a number of model components,
fitting values of the complex impedance to the mathematical model of the sensor to determine values of the number of model components,
identifying one or a functional combination of the model components having a response over time that is substantially insensitive to variations in analyte concentration and sensor sensitivity, and
identifying as stable only sensor output response samples for which the values of corresponding ones of the one or a functional combination of the model components fall within a range of response values using a processor.

11. A method of operating an electrochemical analyte sensor having one or more electrodes, comprising:
applying a time-varying input signal to at least one of the one or more electrodes,
monitoring a time-varying output signal produced by the sensor in response to application of the time-varying input signal,
determining a complex impedance of the sensor based on the time-varying input and output signals,
determining from the complex impedance whether an output response of the sensor is stable, and
producing a signal when the output response of the sensor is not stable by:
selecting a mathematical model of the sensor having a number of model components,
fitting values of the complex impedance to the mathematical model of the sensor to determine values of the number of model components,
identifying one or a functional combination of the model components having a response over time that is substantially insensitive to variations in analyte concentration and sensor sensitivity, and
producing the signal if a number of values of the one or functional combination of the model components fall outside of a range of constant response values using a processor.

12. A method of operating an electrochemical analyte sensor having one or more electrodes, comprising:
applying a time-varying input signal to at least one of the one or more electrodes,
monitoring a time-varying output signal produced by the sensor in response to application of the time-varying input signal,
determining a complex impedance of the sensor based on the time-varying input and output signals,
determining from the complex impedance whether an output response of the sensor is stable, and
executing a sensor calibration procedure if the output response of the sensor is not stable by:
selecting a mathematical model of the sensor having a number of model components,
fitting values of the complex impedance to the mathematical model of the sensor to determine values of the number of model components,
identifying one or a functional combination of the model components having a response over time that is substantially insensitive to variations in analyte concentration and sensor sensitivity, and
executing the sensor calibration procedure if a number of values of the one or functional combination of the model components fall outside of a range of constant response values using a processor.

13. A method of operating an electrochemical analyte sensor having one or more electrodes, comprising:
applying a time-varying input signal to at least one of the one or more electrodes and applying at the same time a constant-value DC input signal to the at least one of the one or more electrodes,
monitoring a time-varying output signal produced by the sensor in response to application of the time-varying input signal,
monitoring a DC output signal produced by the sensor in response to application of the constant-valued DC input signal,
determining a complex impedance of the sensor based on the time-varying input and output signals, and
computing measured values of an analyte to which the sensor is exposed based, at least in part, on the complex impedance by
selecting a model of the sensor having model components,
fitting values of the complex impedance to the model of the sensor to determine complex values of the model components,
determining one or a functional combination of the model components that, when the complex values of the one or functional combination of the model components are mathematically combined with the DC output signal, compensates for an effect on the measured values of the analyte of at least one undesirable characteristic of the DC output signal of the sensor, and
computing the measured values of the analyte based the DC output of the sensor and the one or functional combination of the complex values of the model components using a processor.

14. The method of claim 13 wherein selecting a model of the sensor comprises selecting an equivalent mathematical circuit model of the sensor having model components in the form of mathematical electrical components that are interconnected to define the circuit model.

15. The method of claim 14 wherein fitting the values of the complex impedance to the model of the sensor comprises mathematically fitting the values of the complex impedance to a number of mathematical equations defining the equivalent mathematical circuit model to determine a corresponding set of values for each of the mathematical electrical components.

16. The method of claim 13 wherein determining one or a functional combination of the model components comprises determining one or a functional combination of the model components that, when the values of the one or functional combination of the model components are combined with the DC output signal of the sensor, compensates for an effect on the measured values of the analyte of a sensitivity drift of the DC output signal of the sensor over time.

17. The method of claim 13 wherein computing the measured values of the analyte comprises performing a statistical procedure on the DC output signal of the sensor and on the values of the one or functional combination of the model components.

18. The method of claim 17 wherein computing the measured values of the analyte comprises:
  performing a principle component statistical procedure on the values of the one or functional combination of the model components to determine a number of principle components,
  fitting at least some of the principle components to a set of principle component model equations that model the measured value of the analyte, and
  applying the DC output signal of the sensor to the set of principle component model equations and solving for the measured values of the analyte.

19. The method of claim 17 wherein computing the measured values of the analyte comprises:
  fitting at least some of the values of the one or functional combination of the model components to a set of empirical model equations that model the measured value of the analyte, and
  applying the DC output signal of the sensor to the set of empirical model equations and solving for the measured values of the analyte.

20. A method of operating an electrochemical analyte sensor having one or more electrodes, comprising:
  applying a time-varying input signal to at least one of the one or more electrodes,
  varying a frequency of the time-varying input signal over a spectrum of frequencies,
  monitoring a time and frequency varying output signal produced by the sensor in response to application of the time and frequency varying input signal, and
  determining a corresponding spectrum of complex impedance values of the sensor based on the time and frequency varying input and output signals,
  wherein varying a frequency of the time-varying input signal over a spectrum of frequencies comprises providing the time-varying input signal as a complex mixture of frequencies within the spectrum of frequencies in a manner that allows a magnitude of the time-varying input signal to remain small, and
  determining at least one measured value of the analyte based on the spectrum of complex impedance values of the sensor by:
  selecting a mathematical model of the sensor having a number of model components,
  fitting values of the spectrum of complex impedance values to the mathematical model of the sensor to determine values of the number of model components,
  identifying one or a functional combination of the number of model components having a response over time that produces a sensor response that has minimal undesirable variations in magnitude over time, and
  computing the at least one measured value of the analyte based on values of the identified one or functional combination of the number of model components using a processor.

* * * * *